(12) United States Patent
Kalin et al.

(10) Patent No.: US 7,531,356 B2
(45) Date of Patent: May 12, 2009

(54) PROMOTER SEQUENCES FOR CORTICOTROPIN RELEASING-FACTOR RECEPTOR CRF2α AND METHOD OF IDENTIFYING AGENTS THAT ALTER THE ACTIVITY OF THE PROMOTER SEQUENCES

(75) Inventors: Ned H. Kalin, Madison, WI (US); Patrick H. Roseboom, Madison, WI (US); Charles F. Landry, Madison, WI (US); Steven A. Nanda, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 182 days.

(21) Appl. No.: 11/234,916

(22) Filed: Sep. 26, 2005

(65) Prior Publication Data
US 2006/0025582 A1 Feb. 2, 2006

Related U.S. Application Data

(60) Division of application No. 10/293,702, filed on Nov. 12, 2002, now Pat. No. 7,071,323, and a continuation-in-part of application No. 09/847,852, filed on Apr. 30, 2001, now abandoned.

(60) Provisional application No. 60/338,834, filed on Nov. 12, 2001, provisional application No. 60/201,129, filed on May 2, 2000.

(51) Int. Cl.
*C12N 15/85* (2006.01)
*C07H 21/04* (2006.01)

(52) U.S. Cl. ................ 435/455; 536/24.1; 536/24.5
(58) Field of Classification Search .................. None
See application file for complete search history.

(56) References Cited

U.S. PATENT DOCUMENTS

| | | |
|---|---|---|
| 5,665,543 A | 9/1997 | Foulkes et al. |
| 5,776,502 A | 7/1998 | Foulkes et al. |
| 5,786,203 A | 7/1998 | Lovenberg et al. |
| 5,888,811 A | 3/1999 | Largent et al. |
| 5,965,790 A | 10/1999 | Acton |

OTHER PUBLICATIONS

Sigmund. Viewpoint: Are Studies in Genetically Altered mice Out of Control? Jun. 2000. Arterioscler Thromb. Vasc. Biol. vol. 20. pp. 1425-1429.*
Wall. Transgenic Livestock: Progress and Prospects for the Future. 1996. Theriogenology. vol. 45, pp. 57-68.*
"Researchers Discover DNA Sequence Controlling Obesity Gene," Doctor's Guide to medical & Other News, 1999.
Bakshi VP and Kalin NH, "Corticotropin-Releasing Hormone and Animal Models for Anxiety: Gene-Environment Interactions," Soc. Biol. Psych. 48:1175-1198, 2000.
Bakshi VP, et al., "Reduction of stress-induced behavior by antagonism of corticotropin-releasing hormone 2 (CRH2) receptors in lateral septum or CRH1 receptors in amygdale." J Neurosci 22:2926-2935, 2002.
Bale TL, et al., "Mice Deficient for Corticotropin-Releasing Hormone Receptor-2 Display Anxiety-Like Behaviour and are Hypersensitive to Stress," Nat. Gene. 24:410-414, 2000.
Coste SC, et al., "Abnormal Adaptations to Stress and Impaired Cardiovascular Function in Mice Lacking Corticotropin-Releasing Hormone Receptor-2," Nat. Gene. 24:403-409, 2000.
Eckart K, et al., "Actions of CRF and its analogs," Curr. Med. Chem. 6(11):1035-53, 1999.
Eghbal-Ahmadi M, et al., "Differential Regulation of the Expression of Corticotropin-Releasing Factor Receptor type 2 (CFR2) in Hypothalamus and Amygdala of the Immature Rat by Sensory Input and Food Intake," J. Neurosci. 19(10):3982-3991, 1999.
Grigoriadis DE, et al., "125l-Tyr0-Sauvagine: A Novel High Affinity Radioligand for the Pharmacological and Biochemical Study of Human Corticotropin-Releasing Factor2a Receptors," Am. Soc. Pharmac. Exp. Therap. 50:679-686, 1996.
Grigoriadis DE, et al., "Characterization of Corticotropin-Releasing Factor Receptor Subtypes," Ann. NY Acad. Sci. 780:60-80, 1996.
Harvey M, et al., "Genetic Background Alters the Spectrum of Tumors that Develop in p53-deficient Mice," FASEB J. 7:938-943, 1993.
Kageyama K, et al., "Regulation of Corticotropin-Releasing Factor Receptor Type 2β Messenger Ribonucleic Acid in the Rat Cardiovascular System by Urocortin, Glucocorticoids, and Cytokines," Endocrinology 141(7):2285-2293, 2000.
Kishimoto T, et al., "Deletion of Crhr2 Reveals an Anxiolytic Role for Corticotropin-Releasing Hormone Receptor-2," Nat. Gene. 24:415-419, 2000.
Kostich WA, et al., "Molecular Identification and Analysis of a Novel Homan Corticotropin-Releasing Factor (CRF) Receptor: The CRF2? Receptor," Molec. Endo. 12(8):1077-1085, 1998.
Liaw CW, et al., "Cloning and Characterization of the Human Corticotropin-Releasing Factor-2 Receptor Complementary Deoxyribonucleic Acid," Endocrinology 13:72-77, 1996.
Lovenberg TW, et al., "Cloning and Characterization of a Functionally Distinct Corticotropin-Releasing Factor Receptor Subtype from Rat Brain," Proc. Natl. Acad. Sci. USA 92:836-840, 1995.
Lovenberg TW, et al., "CRF2a and CRF2β Receptor mRNAs are Differentially Distributed Between the Rat Central Nervous system and Peripheral Tissues," Endocrinology 136(9):4139-4142. 1995.
Makino S, et al., "Altered Expression of Type 2 CRH Receptor mRNA in the VMH by Glucocorticolds and Starvation," Am. Physiol. Soc. R1138-R1145, 1998.

(Continued)

*Primary Examiner*—Celine X Qian
(74) *Attorney, Agent, or Firm*—Quarles & Brady LLP

(57) ABSTRACT

The DNA sequences of human and rat $CRF_{2\alpha}$ receptor promoters are disclosed. Certain functional fragments of the human $CRF_{2\alpha}$ receptor promoter are also disclosed. Further disclosed are a method of identifying functional fragments of human and rat $CRF_{2\alpha}$ receptor promoters and a method of identifying agents that can alter the activity of the human or rat $CRF_{2\alpha}$ receptor promoter.

2 Claims, 14 Drawing Sheets

OTHER PUBLICATIONS

Owens MJ and Nemeroff CB, "Physiology and Pharmacology of Corticotropin-Releasing Factor," Pharmac. Rev. 43(4):425-472, 1991.

Radulovic J, et al., "CRF and CRF Receptors," Results and Problems in Cell Differentiation, 26:67-90, 1999.

Radulovic J, et al., "Modulation of Learning and Anxiety by Corticotropin-Releasing Factor (CRF) and Stress: Differential Roles of CRF Receptors 1 and 2," J. Neurosci. 19(12):5016-5025, 1999.

Reul JM, Holsboer F "Corticotropin-releasing factor receptors 1 and 2 in anxiety and depression," Curr Opin Pharmacol 2:23-33, 2002.

Sakai K. et al., "The Genomic Organization of the Human Corticotropin-Releasing Factor Type-1 Receptor," Gene 129:125-130, 1998.

Sánchez MM, et al., "Autoradiographic and In Situ Hybridization Localization of Corticotropin-Releasing Factor 1 and 2 Receptors in Nonhuman Primate Brain," J. Compar. Neurol. 408:365-377, 1999.

Sigmund CD, et al., Viewpoint: Are Studies in Genetically Altered Mice Out of Control?, Arteriosclero, Throm Vasc. Biol. 20:1425-1429, 2000, American heart Assoc., Inc.

Speiss J, et al., "Molecular Properties of the CRF Receptor," TEM 9(4):140-145, 1998.

Steckler T and Holsboer F, "Corticotropin-Releasing Hormone Receptor Subtypes and Emotion," Soc. Biol. Psych. 46:1480-1508, 1999.

Takahashi LK, et al., "Antagonism of CRF(2) receptors produces anxiolytic behavior in animal models of anxiety," Brain Res 902:135-142, 2001.

Tsai-Morris CH, et al., "The Genomic Structure of the Rat Corticotropin Releasing Factor Receptor," J. Biol. Chem. 271(24):14519-14525, 1996.

Wall RJ, "Transgenic Livestock: Progress and Prospects for the Future," Theriogenology 45:57-68, 1996.

Waterson RH, "Homo Sapiens PAC Clone RP5-1143H19," Gene Bank Acession No.: AC004976, Jun. 12, 1998.

Zobel AW, et al., "Effects of the high-affinity corticotropin-releasing hormone receptor 1 antagonist R121919 in major depression: the first 20 patients treated." J Psychiatr Res 34:171-181, 2000.

* cited by examiner

```
         ||||||| || || ||                       | ||||||
-2299 GAOCTGTAAAATCAATTCTTCCCAAACTGCTACTTTTTCTAGTTTTGCC -2260

-1701 TACTTAACATCACGAATCATGTACCAGCTGTGCCTGTAAACATGATAT.T -1653
        |   |  ||||| ||||| |      ||  ||||||||  |||   || | ||
-2249 TCTGTCACATCTCGAATGA.....CAACTGTGCCTATAATAATAAGATCC -2205

-1653 ATGAAGAAATGGTGACATGTCCTAGGATCCTAGTAGTCT.......... -1614
        ||||||||||||    ||   |||    ||    |||  |  |||||
-2204 ATGAAGAAATGCCCCCACATCCAGGGGACCTCG.GGTCTGTGGTCTGTG -2156

-1613 ..TAAGTATTCATA..........CATTTAGGGTGCACAGTAGCTTTTG -1576
         || ||   ||| |              |||| ||| ||||  |  ||| ||||
-2155 GGTATGTGCTCAGACCCAACTGCTCATTCAGGATGCAGAACAGCCTTTG -2106

-1575 GTCCTGACACTGAAGTGGTCACTTTCCAGAGAAACTCTGTCA....... -1534
        |||  |||||||  ||||||||  |||||  |||  ||  ||  ||
-2105 ACTCTGCCGCTGAAATGGTCACTTCCCAGAAGAATCTTTGGTATGTGAGC -2056

-1533 .........AGCAAGCAAG.TTACCCAGTCC......CTATTCTGT -1494
                    ||||| | ||  ||||||||| ||       || |||||
-2055 TCTCCCAGTTAAGAGCAATCCAGTTCACCCAGGCCAACCCTCTGTTCTGC -2006

-1503 AGAAATCTGCATGTAAAAGCGTAGGTCAGAAGT............. -1471
        ||||||||||||||        ||  |  |||||||
-2005 AGAAATCTGCATG........AGATGAGAAGTCCCTGCCTCTGGTCAT -1965

-1470 .....GCTCACCACCTCCTTACTGTGGTATGTGTCTGCTGAGCCATGGCT -1426
             || ||||||||| | ||
-1964 TGGGAGCACAGCCACCTCTTGAC........................... -1943

-1425 CTGATTAGGAATAAAGTCACCCGGGGCTGGGGATTTAGCTCAGTGGTAGA -1376
                        |||             ||||    | |||
-1942 ...........ATA.............GCTGCATCTATAG.......... -1927

-1375 GTGCTAGGAGGCGCAAAGCCCTGGGTTCGGTCCCCAGCTCCGAAAAAAAG -1326
        |||||   |||| || |  ||| |||  | |  |||
-1926 GTGCT.TTAGGCACCA...CCTAGGTAGTAGCTGCAG............ -1894
                                    -1906
-1325 AACCAAAAAAAAAAAAAAAAAAAAGAA.ATAAACTCACCCTTTGCACTTGA -1277
                       ||  || |||||| |   || |   ||| ||       ||
-1893 ...........TAATGAACAAGGATAATAACTTAAGCTTGGCTTAGGA -1857

-1276 ATTGTTTCCTTCTTCT.......CTGTGCTATGACAGTATATGAAGGG -1235
        ||   | ||||| |||            | ||||| ||        ||||||
-1856 TTT..CTCCCTTCCTCTGTGCTGCACCCGCTGG.........TGAAGCG -1817

-1234 CCATCCTTTGCTAGTGAAGGAGACTGCATCCCTGTGA......GGACGGA -1191
        | ||||  |||   |||  |||   |||        ||||||||  || | ||
-1816 CTATCCCTTGTATATGAGGGACACTATTGCCCTGTGAATACATGGGCTGA -1767
```

```
-778   .........AGTCAGGAAGGCTCTTGCCTCAGGCAACATGACA...GAAA  -741
          ||   | |||  ||  ||||| || | |||| ||   || |
-1143  GCTCCAGAAGAGAGGCAAGCCATCCTGCCTGGGGTACCATGGCAGGGAGA  -1094

-740   AGAGAGGCA..........AAACCGCATCCAGACTGGAAAAAAAAACA  -702
        |||| ||            |||  ||| || ||  |||||  |
-1093  GCAGAGTCAGAGGCTGGACCAAAATGCAGCCTGAGTGGAAGCA.......  -1051

-701   CCTAGGCAGGTTCCTCAACCTAGGCC.........................  -676
         |  ||| | || |||||
-1050  ..........TGCCTTACCCCAGGCCCTGCTTCCCAGCCCAATGCCCCA   -1020

-675   .........CATCCACAAGTTATAGGCCCACCCTGAGCCACTCTACAGCGTG  -635
                ||  |||||    ||||||  |||||  ||||||||   |||||
-1019  CTCAGCTGGCAGACAG...CAGGCCCGCCCTGGCCACTCT.GAGCGTG   -965

-634   C..........TCACC..................................  -629
       |          |||||
-964   CAGCCCACAAGCATCACCAAGGAGCATTCTGGCCAGGGTGGGGTGGGG   -915

-628   .................................CCTCCATTCTTG....  -617
                                         ||||||  | |||
-914   GGCCTGGGCAAGTTCTCTGGGGAGGTTCCAGCTCCTCCACACCTGCTGT  -865

-616   ......TGACTTTTCTCCACTCC..........................  -600
             |||    ||||||  | ||
-864   GGGGCCTGA...TTCTCCCGCCCCTGCCCCGCTACTGTTGTGAAAGCA  -818

-599   ...TCAGAT..AGCCCTGCTTAAGCCAGGAG..AAAGAGACCTGTTTTCA  -557
          |||| |  |||||||| |||||  |||  | ||||||   ||  |||
-817   GGGTCAGGTGAAGCCCTGCCCAAGGCTTGAGGAAGAGAGACACATTCTCA  -768

-556   CCTC.....TCACTCTATCTGGTGCCAGGATACTAAACC........AT  -519
       |||       | ||| || ||||||||| | ||||| |         ||
-767   CTTCTTCCTTTATTCTTTCTGGTGCCAAGGCACTAACAACTGGGTGTAT  -718

-518   CAAGTCTTCCAGATAATTTTAATTAATGTCT.TCCTAGATATTCTCATCT  -470
       |||  ||||||||||||||| |   ||| |||  |||||| || |||
-717   AAAGCCTTCCAGATAATTCAGCCAATTCTCCCTAGACTTACTC....   -672

-469   CGCTGCTG.....GTGCCAAATCTG.....GCCGTGTGAAATCTGCCTT  -430
        |  |||      ||||   | |         |  || |  ||| |||
-671   ..CATCTGATTAAATGGCCACCCAGTCACTCAAGCAGGAGACCTGATGTT  -624

-429   GTCACCAGTTCCTGGCTCCTCCTGAGACCATCTACCTACTCCATATTTT  -380
         ||    ||   |||||||  |  |  ||| | ||| |||||| |  ||
-623   ATCCCTGCCTCTGGCTCCTACTTAAACCAGCCACCCACTCC..AGTTC   -576

-379   CTCC..........................ATCTCT............  -370
       ||||                          |||||
-575   CTCCTCACCAGGTCTGGCTGCCCCTCCGAAATCTCTCTCCATTCCAGCTT  -526
```

```
 36 TTGGCCAAGCTGCTAGAAGTGATCCGATTGAGAGC.............. 70
    |  | |||||||            ||   |||| |||
 36 GTCCGGGAAGTCC..........GCACTTGACAGCTCTGGCCACCGGAG  75

71 ..GGCGGCCCCAAAGCTGCCGGGCTGCCCGGGG.TGGGCCGGCAGGCACCT 117
      ||||||| || |||||| ||  |   |||||  ||||| || ||  ||
 76 GTGGCGCCCAAAGCTGCCCGGGAGATCGGGCTGGGCTGCCGGGCCCA  125

118 GGACGCTGCACTCTCT..GGTGGCTCCGGGTCCGGCGAGGTCCCTCGCAGT 166
    |||| | || | |||| ||   ||||  |||||  |  ||||||||||
126 GGACCCCGCGGCCCTCTCGGCCGCTCACTGTCGCCGTCCACTCCCTCGCAGT 175

167 CACGGCGGCGGCCACTCCCACTCC...CAACGCGCCGGCTCCGGAGCGC 214
    |||||  |||||||||||||||||||    |||  |||||| ||| |||
176 CACGGCGGCGGCCACTCCCACTCCCTCTCCCACGCCGGCTGCCGGACGC 225

215 AATGGACGCCGGCCGCTGCTGCTCAGCCTGCTGGAGGCCAACTGCAGCCTGG 264
    |||||||||| |||||||  ||||||||||||||||||||||||||||||||
226 GATGGACGCCGCCGCTGCTGCCAGCCTGCTGGAGGCCAACTGCAGCCTGG 275

265 CACTGGCCCGAAGAGCTGCTTTTGGACGGCTGGCGGAGGCCCCCGGACCCC 314
    | |||||  ||||||||||||| ||||||||||||      |||| |||||||
276 CGCTGGCTGAAGAGCTGCTCTGGACGGCTGGCGGCCACCCCTGGACCCC 325

315 GAAG  318
    || |
326 GAGG  329
```

FIG. 2 (continued - 7)

PROMOTER SEQUENCES FOR CORTICOTROPIN RELEASING-FACTOR RECEPTOR CRF2α AND METHOD OF IDENTIFYING AGENTS THAT ALTER THE ACTIVITY OF THE PROMOTER SEQUENCES

CROSS-REFERENCE TO RELATED APPLICATION

This application is a divisional application of U.S. patent application Ser. No. 10/293,702, filed on Nov. 12, 2002, now U.S. Pat. No. 7,071,323 which claims the benefit of provisional application Ser. No. 60/338,834, filed on Nov. 12, 2001 and is a continuation-in-part application of U.S. patent application Ser. No. 09/847,852, filed on Apr. 30, 2001 now abandoned, which claims the benefit of provisional patent application Ser. No. 60/201,129, filed on May 2, 2000.

STATEMENT REGARDING FEDERALLY SPONSORED RESEARCH OR DEVELOPMENT

This invention was made with United States government support awarded by the following agencies: NIH MH40855. The United States has certain rights in this invention.

BACKGROUND OF THE INVENTION

In modem society stress and its consequences are prevalent and result in considerable distress, alterations in physical health and social and occupational functioning. At its extreme, stress can lead to disabling neuropsychiatric problems which include depression, anxiety disorders, post-traumatic stress disorder and other illnesses (Mitchell, 1998; Arborelius et al., 1999). Recent studies demonstrate the potent effects of stress on the body and brain. For example, chronic and intense stress can result in alterations in the region of the brain that plays an important role in memory (McGaugh and Roozendaal, 2002). In addition, stress can negatively impact cardiovascular function, immune function and gastrointestinal physiology (Tache et al., 2001; Beglinger and Degen, 2002; Coste et al., 2002; Vanitallie, 2002).

It is estimated that 10% of the population suffers from depression and another 15% from clinically significant anxiety. This high incidence of stress-related problems is reflected by the fact that approximately 50% of visits to primary care doctors are stress and/or psychologically related.

Current treatments for stress and its disorders are highly sought after and include the traditional anti-anxiety drugs like Valium and Xanax. More recently newer antidepressants like Prozac have been used to treat depression, anxiety and other stress related problems. It is estimated that $6 billion was spent last year in the U.S. on drugs like Prozac. However, these treatments still suffer from lack of efficacy in approximately 30% of individuals and in those that do respond only roughly 50% of them will return to normal function. In addition, these treatments have bothersome side-effects (50% have marked sexual dysfunction) which make treatment with these drugs unacceptable for many individuals. Since depression and anxiety are recurrent and chronic disorders it is important that patients are comfortable taking their medication over a long period of time. Overactivity of the corticotropin-releasing factor CRF system is implicated in depression and anxiety and treatments aimed at this system may be very effective (Reul and Holsboer, 2002). Treatments targeting this system, based on preclinical evidence, offer a completely new and promising approach for treating stress-related illnesses.

BRIEF SUMMARY OF THE INVENTION

In one aspect, the present invention relates to an isolated nucleic acid that contains the full length or a functional fragment of the human or rat $CRF_{2\alpha}$ receptor promoter. By functional fragment, we mean a fragment of the human or rat $CRF_{2\alpha}$ receptor promoter that retains the ability to drive expression of a reporter gene in a host cell to at least twice as that of the house keeping level. The housing keeping level is defined as the expression level of the same reporter gene in the same host cell and under the same conditions without a promoter sequence. Preferably, a functional fragment used in the nucleic acids, vectors, cells and methods of the present invention has the ability to drive expression of a reporter gene to at least three or five times of the house keeping level. The full length human $CRF_{2\alpha}$ receptor promoter is the 3898 bp upstream of the putative transcription start site for the human $CRF_{2\alpha}$ receptor (nucleotides 46 to 3943 of SEQ ID NO:2). The full length rat $CRF_{2\alpha}$ receptor promoter is the 4693 bp upstream of the putative transcription start site for the rat $CRF_{2\alpha}$ receptor (nucleotides 1 to 4693 of SEQ ID NO:1). Examples of functional fragments of the human $CRF_{2\alpha}$ receptor promoter include but are not limited to the 3405 bp (nucleotides.539 to 3943 of SEQ ID NO:2), the 2883 bp (nucleotides 1061 to 3943 of SEQ ID NO:2), the 2346 bp (nucleotides 1598 to 3943 of SEQ ID NO:2), the 1906 bp (nucleotides 2038 to 3943 of SEQ ID NO:2), the 1375 bp (nucleotides 2569 to 3943 of SEQ ID NO:2), the 840 bp (nucleotides 3104 to 3943 of SEQ ID NO:2), the 346 bp (nucleotides 3598 to 3943 of SEQ ID NO:2), the 295 bp (nucleotides 3649 to 3943 of SEQ ID NO:2), the 205 bp (nucleotides 3739 to 3943 of SEQ ID NO:2), and the 104 bp (nucleotides 3840 to 3943 of SEQ ID NO:2) upstream of the putative transcription start site for the human $CRF_{2\alpha}$ receptor.

In another aspect, the present invention relates to a vector that contains a heterologous reporter gene operably linked to the full length or a functional fragment of the human or rat $CRF_{2\alpha}$ receptor promoter. A host cell that contains such a vector is also within the scope of the present invention.

In another aspect, the present invention relates to a method of evaluating the ability of a fragment of the full length human or rat $CRF_{2\alpha}$ receptor to drive transcription. The method involves providing a vector that contains a heterologous reporter gene operably linked to the fragment, introducing the vector into a suitable host cell, and determining the expression level of the reporter gene. The expression level can be determined by measuring the activity of the protein product of the gene. The expression level can also be determined directly by measuring the product of the gene at the mRNA level or the protein level. A negative control should be included for determining the expression level. It is well within the capability of a skilled artisan to set up suitable negative controls for the method of the present invention. For example, a vector that contains the same reporter gene but not operably linked to a promoter can be used as a negative control. Through comparing the expression level of the reporter gene driven by a fragment and that of a negative control, whether the fragment is a functional fragment for purpose of the present invention can be determined.

An isolated nucleic acid that contains a functional fragment of the human or rat $CRF_{2\alpha}$ receptor promoter as determined by the method described above is within the scope of the present invention. Also within the scope of the present invention are a vector that contains a reporter gene operably linked to a functional fragment determined by the method described above and a host cell that contains the vector.

In another aspect, the present invention relates to a method of identifying an agent that can alter the activity of the human or rat $CRF_{2\alpha}$ receptor promoter. The method involves providing a cell that contains a vector in which a reporter gene is operably linked to the full length or a functional fragment of the human or rat $CRF_{2\alpha}$ receptor promoter, exposing the cell to a test agent, and measuring and comparing the reporter gene expression in the cell to that of a control cell that is not exposed to the test agent. A higher or lower expression level in comparison to that of the control cell indicates that the agent can alter the activity of the promoter region of the human or rat $CRF_{2\alpha}$ receptor. Such an agent identified by the method described above is also within the scope of the present invention.

In another aspect, the present invention relates to a method of determining which region of the human or rat CRF2α receptor promoter interacts with a test agent. The method involves providing multiple groups of cells wherein each cell contains a vector in which a reporter gene is operably linked to a fragment of the human or rat CRF2α receptor promoter and wherein the cells of the same group contain the same fragment and the cells in different groups contain different fragments of the human or rat $CRF_{2\alpha}$ receptor promoter, exposing the groups of cells to a test agent, and measuring and comparing the reporter gene expression level of each of the cell groups to that of corresponding control cells that are not exposed to the test agent to determine the effect of the test agent on the promoter activity of different fragments. The effect of the test agent on the promoter activity of different fragments can then be compared.

It is one object of the present invention to identify the promoter region for the human and rat $CRF_{2\alpha}$ receptor.

It is another object of the present invention to provide a method for screening compounds or identifying agents that can alter the activity of the human or rat $CRF_{2\alpha}$ receptor promoter region.

Other objects, advantages and features of the present invention will become apparent after analysis and review of the claims, specification and drawings.

BRIEF DESCRIPTION OF THE SEVERAL VIEWS OF THE DRAWINGS

FIG. 2 is a comparison of the promoter regions for the rat and human $CRF_{2\alpha}$ receptor gene. In the comparison, the upper sequence is the rat (nucleotides 1506 to 5011 of SEQ ID NO:1) and the lower sequence is the human (SEQ ID NO:2). The arrows denote base +1 (transcription start point) in the rat and human sequences (correspond to nucleotide 4694 of SEQ ID NO:1 and nucleotide 3944 of SEQ ID NO:2, respectively). The promoter fragments are numbered in relation to this. The sequences of the primers used to generate the truncated fragments is denoted in underlined italics, and the identity of the primer is listed below the corresponding sequence.

DETAILED DESCRIPTION OF THE INVENTION

A. Definition

Figure 1:
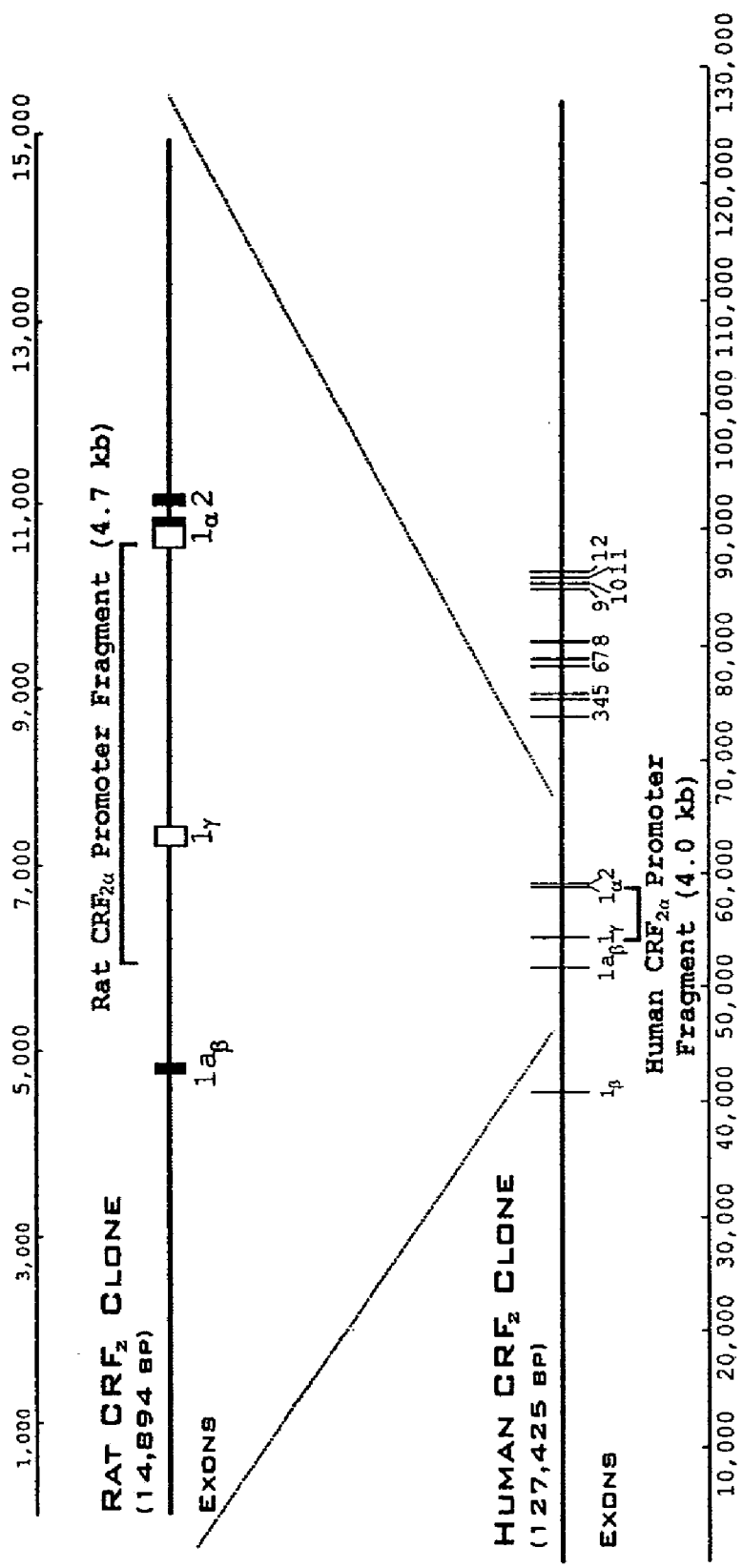
FIG. 1 is the representation of rat and human CRF2 genomic clones.

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as those occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

B. In General

The present invention relates to corticotropin-releasing factor (CRF) (Guillemin and Rosenberg, 1955), which is a hormone and neurotransmitter thought to integrate the various electrophysiological, immune, endocrine and behavioral responses to stress (Arborelius et al., 1999; Takahashi, 2001).

Studies in animals demonstrate that antagonism of the CRF system blocks the distress and physical effects related to stress (Takahashi et al., 2001; Bakshi et al., 2002). Studies in humans show that the CRF system in the brain is overactive in patients with depression, anxiety disorders and other neuropsychiatric problems (Nemeroff, 1989; Chappell et al., 1996; Fossey et al., 1996; Bremner et al., 1997; Mitchell, 1998; Baker et al., 1999). In addition, human and animal studies demonstrate that many effective antidepressant treatments decrease brain CRF activity (Veith et al., 1993). Based on these findings the pharmaceutical industry is currently intensively searching for orally administered compounds that will block or reduce the effects of CRF in the brain. Already some compounds have been identified and are in the early stages of human studies (Zobel et al., 2000).

The CRF system is now known to consist of at least seven components. CRF is a neurotransmitter that is released from neurons and has its effects by interacting with CRF receptors located on adjacent brain cells. Urocortin, urocortin II, and urocortin III are other neurotransmitters similar to CRF that also interact with the system (Vaughan et al., 1995; Lewis et al., 2001; Reyes et al., 2001). Once stimulated the receptors activate intracellular processes which mediate the stress effects.

CRF produces its effects by interacting with two different receptors termed CRF1 and CRF2 (Chen et al., 1993; Perrin et al., 1995). There also exists at least three different splice variants of the CRF2 receptor, termed "$CRF_{2\alpha}$," "$CRF_{2\beta}$," and "$CRF_{2\gamma}$" (Lovenberg et al., 1995a; Kostich et al., 1998). In addition to CRF1 and CRF2 receptors, there also exists a protein, termed CRF binding protein (CRF-BP), that is found in brain cells and functions to inactivate CRF after it is released (Potter et al., 1991).

While much is known about the biology of CRF, considerably less is understood about CRF1, CRF2 and the binding protein. Most believe that the CRF1 receptor is responsible for mediating the effects of stress and also may be important in depression and anxiety. However, other evidence suggests that CRF2 receptor may also play a critical role in mediating the effects of stress (Bakshi et al., 2002). The pharmaceutical industry has targeted CRF1 for the development of antagonists to block the effects of stress. While interest in CRF2 may exist, small molecule antagonists specific for this receptor remain to be discovered.

The present invention invokes a different therapeutic approach aimed at altering the regulation of the gene encoding the CRF2 receptor and has the potential to be a more effective strategy in the treatment of anxiety, depression and other stress-related problems. This approach is based on the hypothesis that the primary problem in these illnesses is disregulation of one or more components of the CRF system. Thus, a treatment aimed at the primary cause of these problems should prove more effective and be without non-specific effects on other systems. For example, drugs that control the regulation of CRF or its receptors would allow greater precision in stress management. Traditional approaches suffer from numerous unwanted effects because receptor antagonists affect all receptors throughout the brain and body and do not selectively interact with those regions that are most important in an illness.

The advantage of understanding and developing drugs to affect regulation of genes that make receptors and other proteins is that they can be directed to alter levels of proteins in specific tissues. For example, the amygdala is located deep in the brain and is thought to be pivotal in mediating the effects of CRF in depression and anxiety. Once the factors that regulate the selective expression of CRF in the amygdala are identified, drugs could be targeted to affect CRF only in this region, leaving other sites (cortex, brain stem, heart, hypothalamus) unaffected.

For the purposes of the present invention we have cloned and identified the promoter region of the rat CRF2 receptor gene. This promoter region of the gene is responsible for determining where in the body and when during development the CRF2 receptor is expressed. This region also controls how much receptor is expressed.

Therefore, we envision that the promoter region would be a target for drug development for the treatment of various psychopathologies described above, including depression, generalized anxiety, social anxiety, post traumatic stress and panic disorder. Using the promoter region of the gene in a cell and/or chip based screening assay will allow us to develop methods to identify agents that alter the activity of the promoter region and, thus, affect the expression of the CRF2 receptor. These agents could have significant therapeutic potential in the treatment of various psychopathologies.

C. Human CRF2 Receptor Gene

The clone containing the entire gene for the human CRF2 receptor was obtained from Research Genetics (Huntsville, Ala.). This PAC clone (RP5-1143H19) contained a 127,425 bp insert, which included the first exons for the $CRF_{2\alpha}$, $CRF_{2\beta}$ and $CRF_{2\gamma}$ receptors and remaining 11 exons that are common to all three isoforms (see FIG. 1). The clone contains approximately 42,000 bp upstream of exon 1 of the $CRF_{2\alpha}$, and approximately 39,000 bp downstream of the final exon.

D. Rat CRF2 Receptor Gene

The rat CRF2 receptor gene was cloned from a Sprague-Dawley rat genomic library constructed in Lambda FIX® II obtained from Stratagene (La Jolla, Calif.). The library was prepared from a partial Sau3A I digest of kidney DNA obtained from male rats (16 months old). The library was probed with a $^{32}P$-labelled fragment of the rat CRF2α cDNA (Lovenberg et al., 1995b), which corresponded to bases 1 to 261 of the cDNA (Genbank # U16253). The single positive clone that was obtained was plaque purified, the insert was excised by NotI digestion and subcloned into the pGEM-5Zf (+) vector (Promega, Madison, Wis.). The entire insert was sequenced using the GPS-1 Genome Priming System (New England Biolabs, Beverly, Mass.) which uses randomly interspersed primer binding sites.

The insert was determined to be 14,894 bp long, and the intron/exon junctions were identified by comparison of the insert sequence to that of rat $CRF_{2\alpha}$ (Genbank # U16253), mouse $CRF_{2\beta}$ (Genbank # U21729) and human $CRF_{2\gamma}$ (Genbank # AF019381) cDNAs. This revealed that the clone contained the first exons of the $CRF_{2\alpha}$ and second exon (1a) of the $CRF_{2\beta}$ (FIG. 1). The clone also contained exon 2, which is common to each of the isoforms. In addition, the clone contained a region that corresponds to the first exon of the $CRF_{2\gamma}$; however, it lacks the necessary consensus splice site sequences and ATG translation start site to function as an exon.

E. Comparison of Rat and Human CRF2 Gene Sequences

Figure 2:
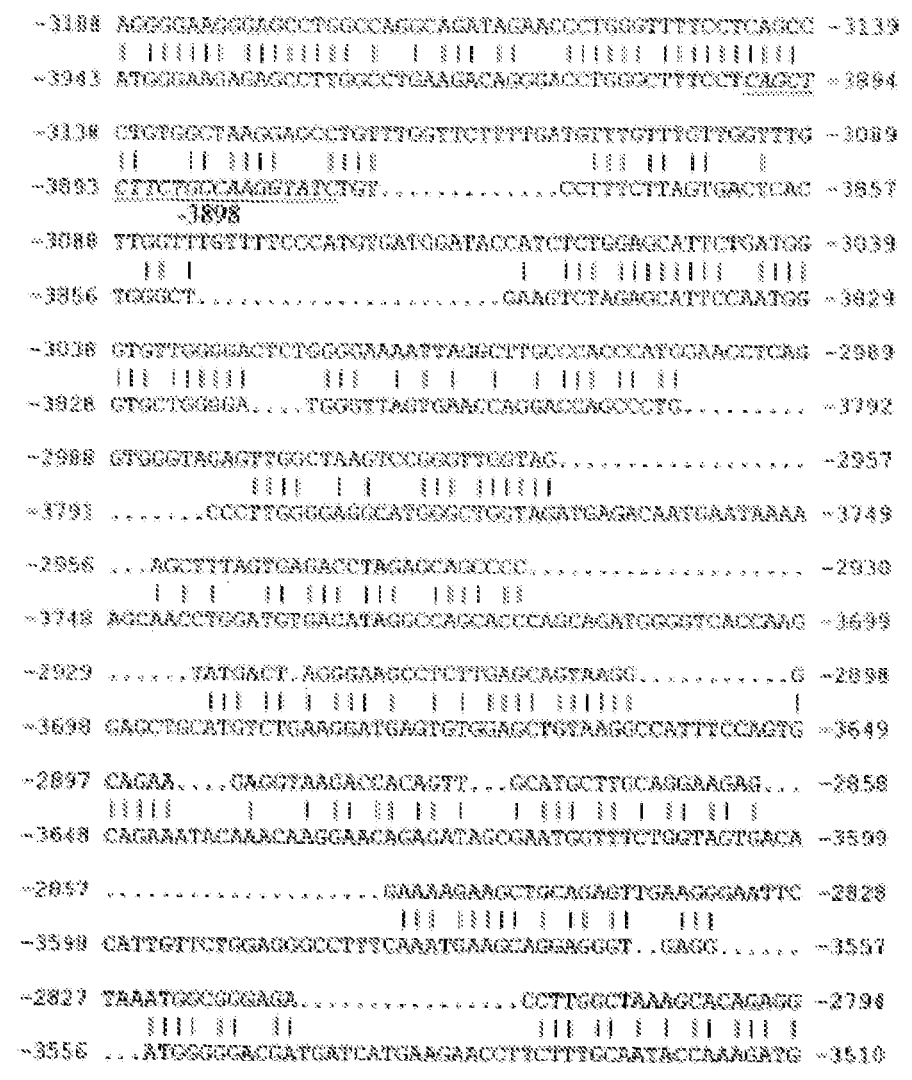
Figure 2:
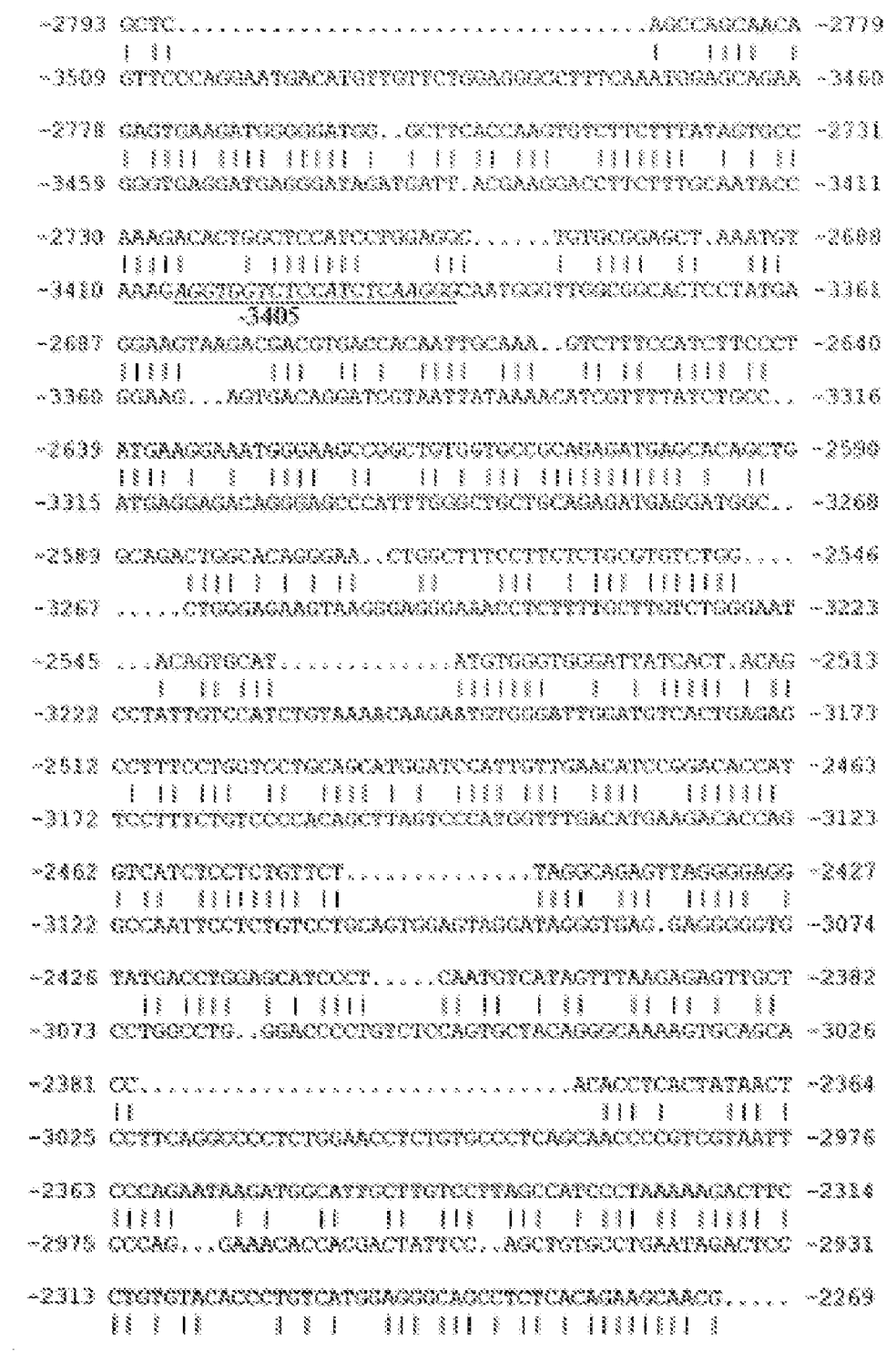
Figure 2:
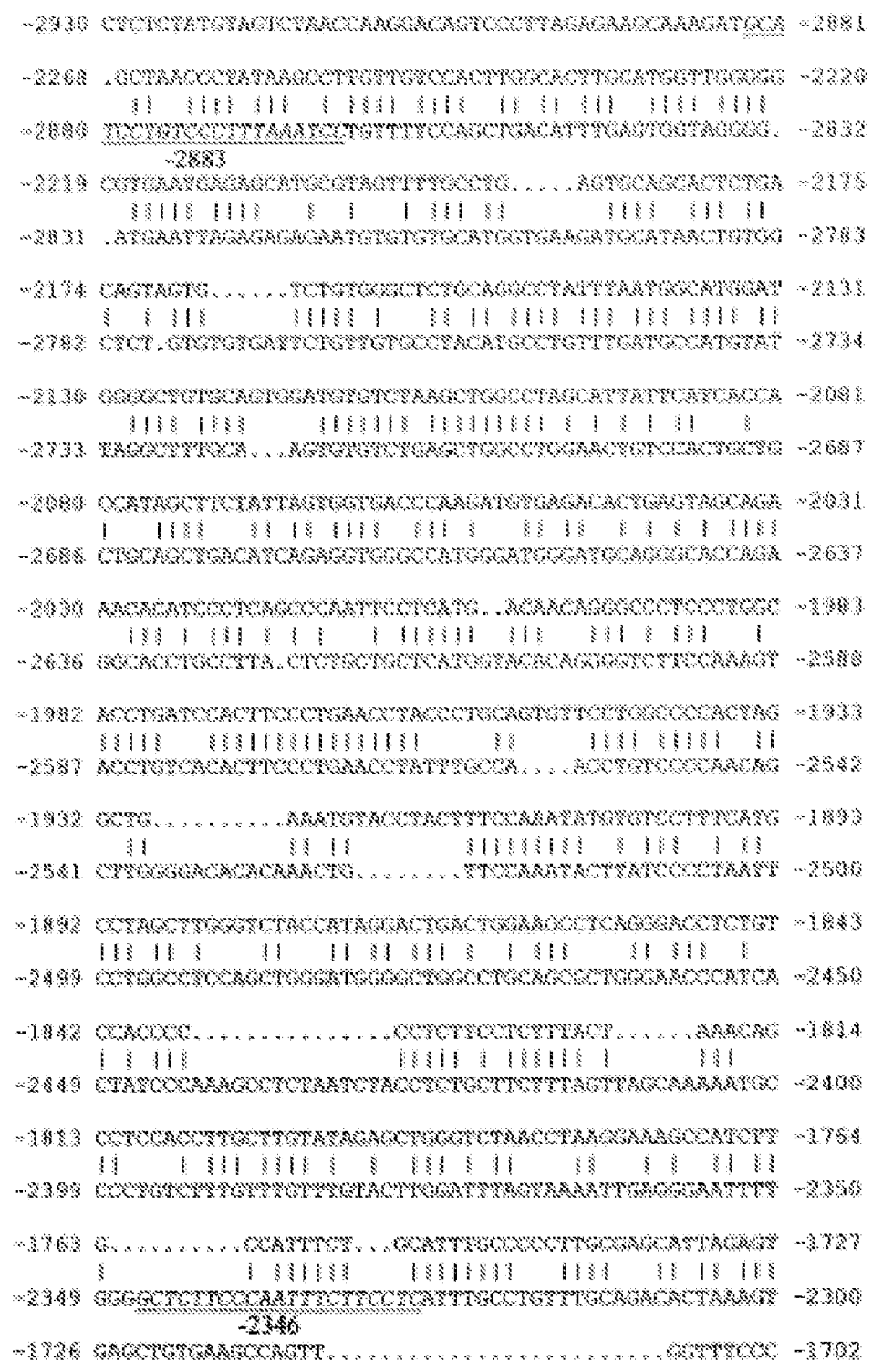
Figure 2:
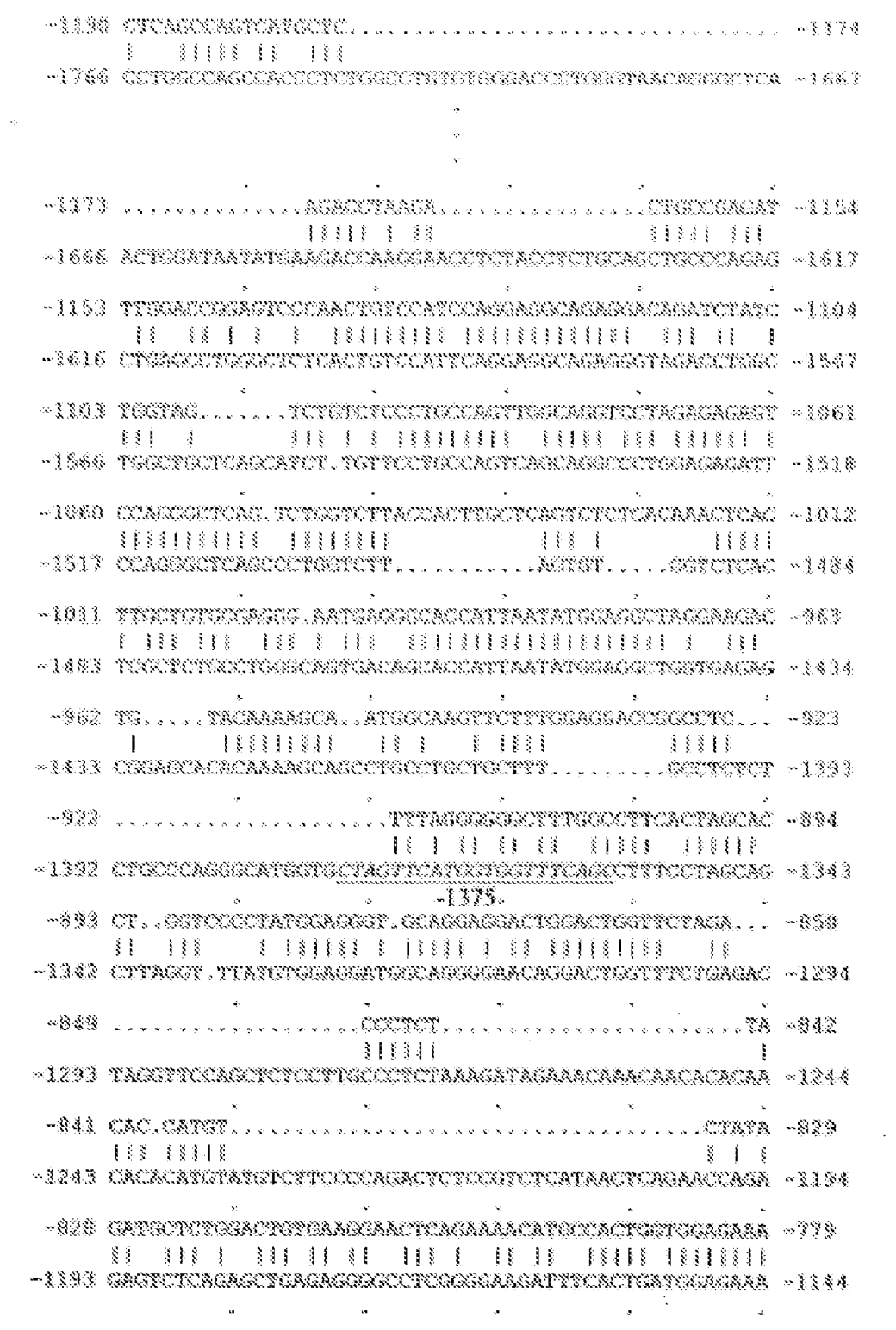
Figure 2:
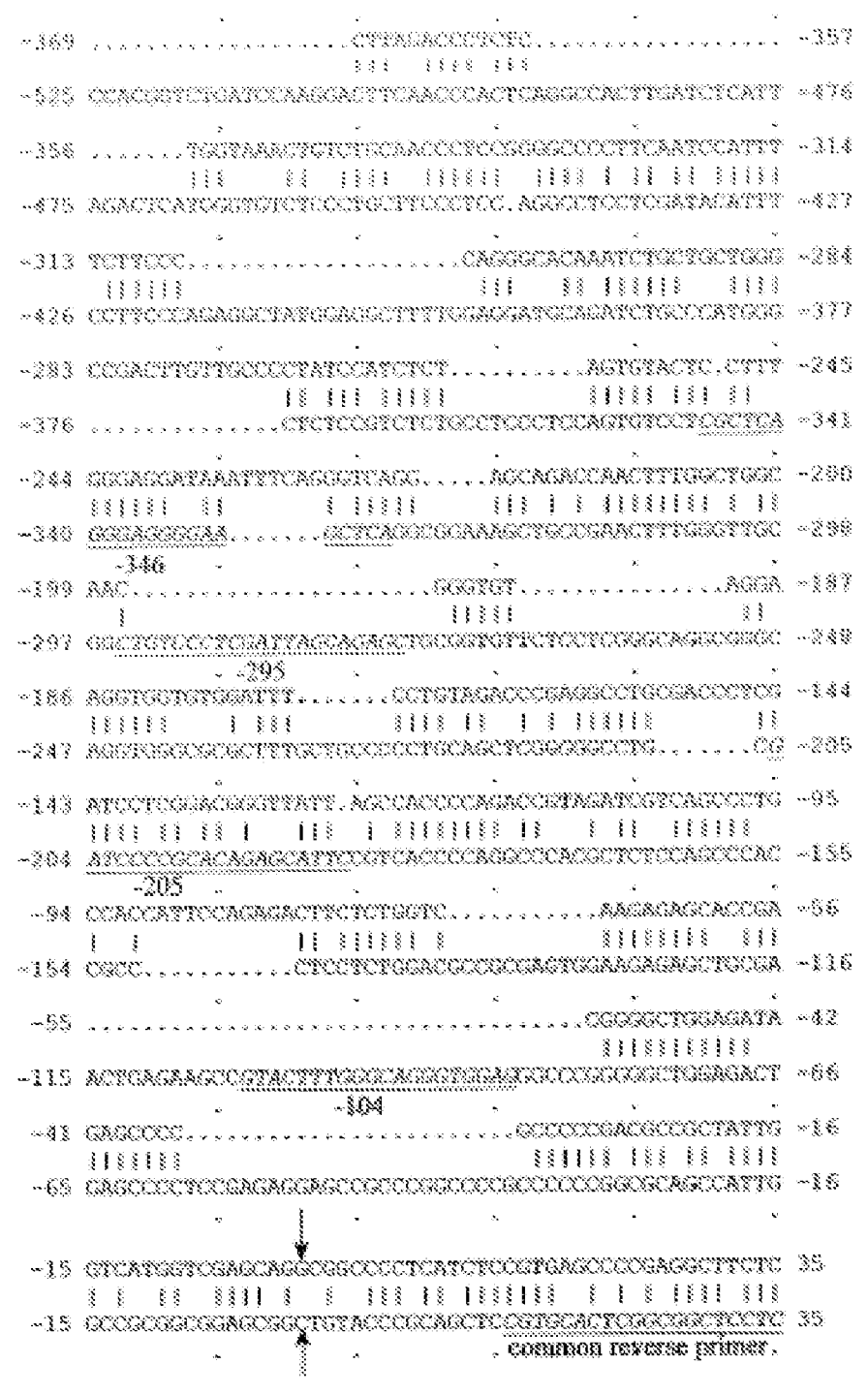

We identified the region of the human CRF2 gene that corresponds to the rat CRF2 genomic clone (see FIG. 1). The promoter region for the $CRF_{2\alpha}$ should be located within the ~4000 bp of sequence that lie upstream of the first exon for the $CRF_{2\alpha}$ but downstream of the first $CRF_{2\gamma}$ exon. We compared the rat and human CRF2 gene sequences in a subregion of this fragment that contains the first 2000 bp immediately upstream of the first $CRF_{2\alpha}$ exon using the BestFit program from the Genetics Computer Group (GCG) Wisconsin Package version 10.0. The gap creation penalty was set at 40 and the gap extension penalty was set at 2. The analysis revealed 70.4% identity between the two sequences (see FIG. 2). It is likely that both mouse and monkey sequences will have greater than 70.4% identity compared to rat and human, respectively.

Transcription factor-binding sites are short sequences of DNA located in promoter regions where transcription factors bind to exert their effect on gene regulation. These sites have been found to confer unique expression properties to genes in other systems and are likely important for the temporal and spatial regulation of the CRF2 receptor gene. They also serve to highlight the basal promoter, which is the region of the CRF2 receptor promoter that is most critical for appropriate developmental and cell-specific expression of the gene.

To identify potential transcription factor binding sites, analysis was performed on 2000 bp of sequence immediately upstream of the first $CRF_{2\alpha}$ exon start site in both the rat and human sequences using MatInspector v2.2 (Quandt et al., 1995), public domain software with the Transfac 4.0 vertebrate matrices (Heinemeyer et al., 1999). The threshold levels were set at 1.0 for core similarity and 0.9 for matrix similarity. This identified 152 and 146 potential transcription factor binding sites in the human and rat $CRF_{2\alpha}$ promoter regions, respectively.

Numerous potential transcription factor binding sites are present within any given promoter sequence. Very few of these are ultimately functionally relevant. A comparison between the same promoter from two different species allows one to identify those elements that are conserved and therefore likely to be critical for the appropriate functioning of the gene. Comparison of the human and rat results revealed 51 putative binding sites that were conserved in terms of location and orientation within the two sequences. These transcription factor-binding sites are listed in Table 1. The location in the table refers to the position of the sequence upstream of the putative transcription start site (+1 in FIG. 2). By convention, positions upstream of the transcription start site are preceded by a minus symbol. The plus and minus symbols in parentheses following the location refer to the sense and antisense strands, respectively. Because these sites are conserved between rat and human we feel they may constitute important regulatory elements.

F. Preparation of $CRF_{2\alpha}$ Receptor Promoter Constructs

The minimal promoter fragment within the human and rat $CRF_{2\alpha}$ receptor genes that confers the correct temporal and spatial expression of the $CRF_{2\alpha}$ receptor will be subcloned into an expression vector that contains either the firefly luciferase (pGL3-basic Promega, Madison, Wis.) or enhanced green fluorescent protein as a reporter (Clontech, Palo Alto, Calif.).

i. Human $CRF_{2\alpha}$ Receptor Promoter

To obtain the fragment corresponding to the promoter region of the $CRF_{2\alpha}$ gene, it was necessary to first subclone into an intermediate vector, pRL-null (Promega, Madison, Wis.) prior to subcloning into the reporter construct that will be used to transfect cells. A 4040 bp fragment of the human CRF2 gene corresponding to the promoter region of the $CRF_{2\alpha}$ receptor (see FIG. 1) was excised with the restriction enzymes NarI and NdeI. The fragment was subcloned into the vector pRL-null that had been digested with the same two enzymes. This insert was then removed from the pRL-null construct with XhoI and EcoRI and subcloned into the pEGFP-1 vector that had been digested with the same two enzymes. We also subcloned this fragment into a luciferase reporter, pGL-3 basic (Promega). The insert was removed from pRL-null with EcoIcRI and SalI and inserted into pGL3-basic that had been digested with SmaI and XhoI.

We focused on the first 2000 bp in our sequence comparison and found a 70.4% identity between the rat and human sequence. Although we will initially examine a fragment containing 3898 bp of sequence, we know that a smaller fragment that has been deleted from the 5' end will function as the basal promoter. Using a common reverse (3') primer that ended 36 bp downstream of the putative transcription start point (TSP), we generated sequentially smaller fragments of the $CRF_{2\alpha}$ promoter region through PCR with several forward (5') primers. The putative TSP has been clearly identified in FIG. 2 and it's relative location is +1. Please note that in this standard nomenclature system there is no zero position. The constructs generated were from −3898, −3405, −2883, −2346, −1906, −1375, −840, −346, −295, −205, and −104 bp relative to the putative TSP through +36 bp (referred to as the −3898, −3405, −2883, −2346, −1906, −1375, −840, −346, −295, −205, and −104 constructs respectively). Our goal is to define the basal promoter, which in some instances has been found to be shorter than 500 bp.

ii. Rat $CRF_{2\alpha}$ Receptor Promoter

A 4693 bp fragment corresponding to the promoter region of the rat $CRF_{2\alpha}$ receptor (see FIG. 1) can be obtained by digestion with HindIII and BsrBI. This can be subcloned into the HindIII and SmaI sites of the pEGFP-1 vector. This fragment can also be subcloned into a luciferase reporter, pGL-3 basic (Promega). To generate smaller fragments of the rat $CRF_{2\alpha}$ promoter, a strategy identical to that described for the human $CRF_{2\alpha}$ promoter can be used. The ability of each fragment to drive transcription can be determined as described below.

TABLE 1

Location of conserved putative transcription factor binding sites. Numbering is in relation to the putative transcription start sites noted as +1 in FIG. 2. The (+) and (−) indicate that the sequence is present in the sense or antisense strand, respectively.

| Binding Site Name | Position (strand) of Binding Site | |
| --- | --- | --- |
| | Rat | Human |
| AP1FJ_Q2 | −1870 (+) | −1771 (+) |
| AP1FJ_Q2 | −1574 (+) | −1468 (+) |
| AP1FJ_Q2 | −1542 (−) | −1544 (−) |
| AP1FJ_Q2 | −1299 (−) | −1093 (−) |
| AP1FJ_Q2 | −434 (−) | −654 (−) |
| AP1FJ_Q2 | −109 (−) | −189 (−) |
| AP1_Q2 | −1564 (−) | −1544 (−) |
| AP1_Q2 | −434 (−) | −654 (−) |
| AP1_Q2 | −109 (−) | −189 (−) |
| AP4_Q5 | −1679 (+) | −1631 (+) |
| AP4_Q5 | −1679 (−) | −1631 (−) |
| AP4_Q5 | −269 (−) | −280 (−) |
| CREB_02 | −108 (−) | −188 (−) |
| DELTAEF1_01 | −1986 (−) | −1956 (−) |
| DELTAEF1_01 | −1812 (+) | −1916 (+) |
| DELTAEF1_01 | −899 (+) | −877 (+) |
| DELTAEF1_01 | −189 (−) | −250 (−) |
| E47_02 | −901 (−) | −879 (−) |
| GATA1_02 | −1663 (+) | −1667 (+) |
| GATA1_02 | −601 (+) | −711 (+) |
| GATA1_03 | −512 (+) | −711 (+) |
| GATA1_03 | −273 (−) | −629 (−) |
| GATA1_04 | −600 (+) | −710 (+) |
| GATA1_04 | −551 (−) | −629 (−) |
| GATA1_05 | −510 (+) | −709 (+) |
| GATA_C | −508 (+) | −707 (+) |
| GC_01 | −41 (−) | −42 (−) |
| GKLF_01 | −1836 (−) | −1851 (−) |
| IK2_01 | −1974 (−) | −1986 (−) |
| IK2_01 | −1857 (+) | −1967 (+) |
| IK2_01 | −1709 (−) | −1817 (−) |
| IK2_01 | −1210 (−) | −1232 (−) |
| IK2_01 | −1004 (+) | −1103 (+) |
| IK2_01 | −314 (−) | −296 (−) |
| LMO2COM_01 | −899 (−) | −877 (−) |
| LMO2COM_02 | −549 (−) | −627 (−) |
| MYOD_01 | −899 (−) | −877 (−) |
| MYOD_Q6 | −898 (+) | −876 (+) |
| MZF1_01 | −1400 (+) | −1321 (+) |
| MZF1_01 | −1345 (−) | −1228 (−) |
| MZF1_01 | −889 (−) | −852 (−) |
| MZF1_01 | −310 (−) | −203 (−) |
| NF1_Q6 | −210 (+) | −20 (+) |
| NFAT_Q6 | −1274 (−) | −1356 (−) |
| NFAT_Q6 | −719 (+) | −829 (+) |
| NFAT_Q6 | −177 (−) | −432 (−) |
| NFY_01 | −25 (−) | −25 (−) |
| NFY_Q6 | −22 (−) | −22 (−) |

TABLE 1-continued

Location of conserved putative transcription factor binding sites. Numbering is in relation to the putative transcription start sites noted as +1 in FIG. 2. The (+) and (−) indicate that the sequence is present in the sense or antisense strand, respectively.

| Binding Site Name | Position (strand) of Binding Site | |
|---|---|---|
| | Rat | Human |
| NKX25_01 | −1283 (−) | −489 (−) |
| S8_01 | −509 (−) | −708 (−) |
| SP1_Q6 | −40 (−) | −41 (−) |

G. Production of Transfected Cell Lines

In one embodiment, the present invention is a transfected cell line. One preferred method of creating such a cell line is described as follows: The constructs described above containing the human or rat promoter fragments placed upstream of the firefly luciferase gene are used to transfect immortalized cell lines. The constructs are transfected into CHO-K1 and A7R5 cell lines using lipofectamine 2000 (Life Technologies, Rockville, Md.). The CHO-K1 cells are not known to express CRF receptors whereas A7R5 cells, derived from aortic cells, have been demonstrated to express CRF receptors. Both cell lines can be maintained at 37° C. with 5% $CO_2$ in DMEM supplemented with 10% fetal bovine serum. Primary cultures of the central nervous system, as well as additional immortalized cell lines, are also appropriate for these transfections. To control for transfection efficiency, the cells are also co-transfected with the pRL-TK vector (Promega, Madison, Wis.). The pRL-TK vector contains the *Renilla luciferase* gene downstream of the herpes simplex virus thymidine kinase promoter, a promoter which provides low to moderate levels of expression. Cell lysates are assayed for total protein using the BCA assay (Pierce, Rockford, Ill.) to standardize for the protein extraction. The level of reporter gene expression from a standardized amount of cell extract is quantified by measuring luciferase activity using a luminometer (EG&G Wallac, Gaithersburg, Md.) and the dual-luciferase reporter assay system (Promega, Madison, Wis.). Firefly luciferase activity reflects $CRF_{2\alpha}$ receptor promoter activity and Renilla luciferase activity is used to normalize data between experiments.

H. Characterization of Basal Expression from $CRF_{2\alpha}$ Receptor Promoter Fragments Using the methods described above, transient transfections of CHO-K1 and A7R5 cultures were assayed for reporter gene expression (See FIG. 3 and FIG. 4). In these experiments, three basic controls were utilized. The cultures referred to as pGL-3 basic were transfected with a pGL-3 firefly luciferase reporter construct that did not contain an experimental promoter, and with the pRL-TK vector. These cultures should demonstrate a very low level of expression and may be considered a negative control. The cultures referred to as pGL-3 control were transfected with a construct containing the firefly luciferase reporter downstream of the SV40 viral promoter as well as the pRL-TK vector. These cultures should demonstrate a very high level of expression and may be considered a positive control. Finally, the cultures referred to as unrelated DNA were transfected with a construct containing 1916 bp of DNA sequence upstream of the firefly reporter gene and with the pRL-TK vector. The 1916 bp of this construct were a random DNA sequence with the final 21 bp most 3' being identical to our putative promoter constructs. These cultures were intended to demonstrate the specificity of our promoter constructs.

Figure 3:
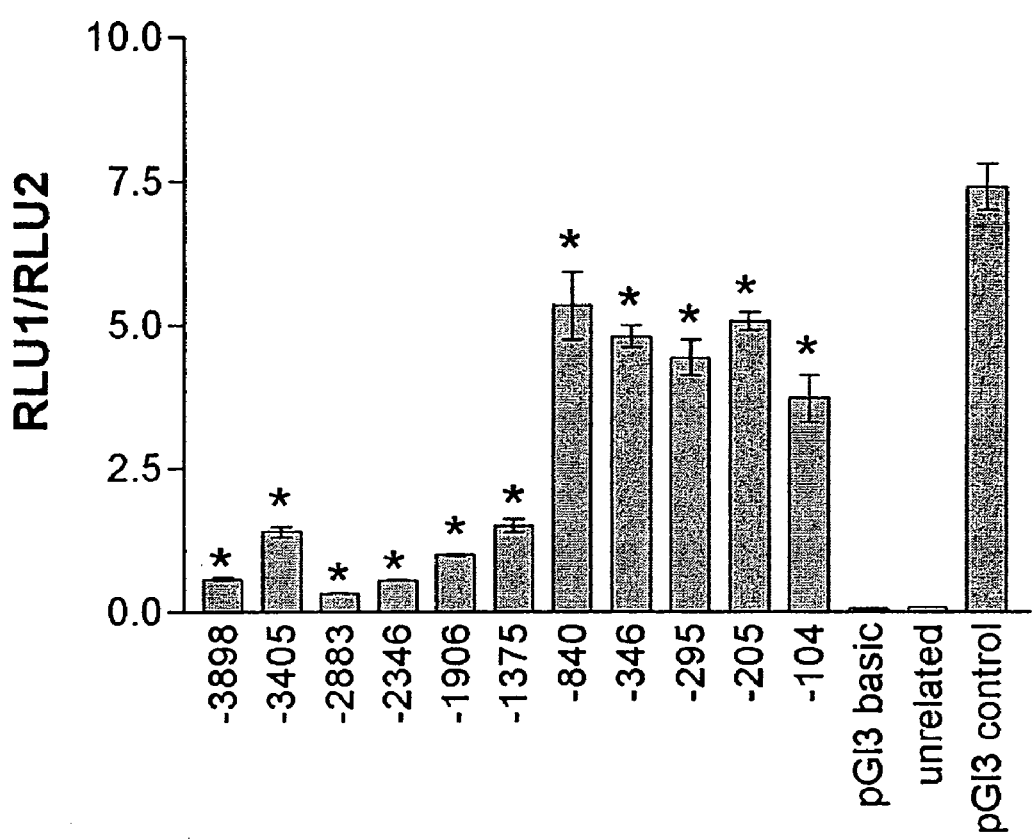
FIG. 3 shows basal expression from various $CRF_{2\alpha}$ receptor promoter fragments in CHO-K1 cells.

Our results in the CHO-K1 cultures indicate that the −840, −346, −295, −205, −104 constructs have the highest levels of expression of the $CRF_{2\alpha}$ promoter constructs (See FIG. 3). Distal regions of the $CRF_{2\alpha}$ promoter appear to exert an inhibitory influence that is gradually unmasked as the length of the promoter is shortened, reaching a plateau beginning with the −840 construct that appears to last through the shortest promoter construct. 1-way ANOVA revealed a significant difference amongst constructs (F=124, P<0.0001). Planned pairwise comparisons using Student's t-tests indicated that all the constructs were significantly higher than the pGL3-basic control construct (*, p<0.0001). Examination of the mean indicates that our lowest level of expression (−2883 construct) is 378% greater than housekeeping levels of expression (pGL-3 basic) (mean−2883=0.330±0.009, mean pGL3 basic=0.069±0.004), and is 4% of the expression elicited by the viral SV40 promoter (pGL-3 control) (mean−2883=0.330±0.009, mean pGL3 control=7.433±0.401). Our highest level of expression (−840 construct) is 7657% greater than expression from the promoterless control vector (pGL-3 basic) (mean −840=5.353±0.596, mean pGL3 basic=0.069±0.004), and is 72% of the strong expression from the SV40 promoter (pGL-3 control) (mean−840=5.353±0.596, mean pGL3 control=7.433±0.401). Furthermore, an unrelated human chromosomal DNA sequence (unrelated) was not able to drive expression above background (FIG. 3). Thus, the $CRF_{2\alpha}$ promoter constructs function and are appropriate tools to monitor $CRF_{2\alpha}$ specific transcription.

Figure 4:
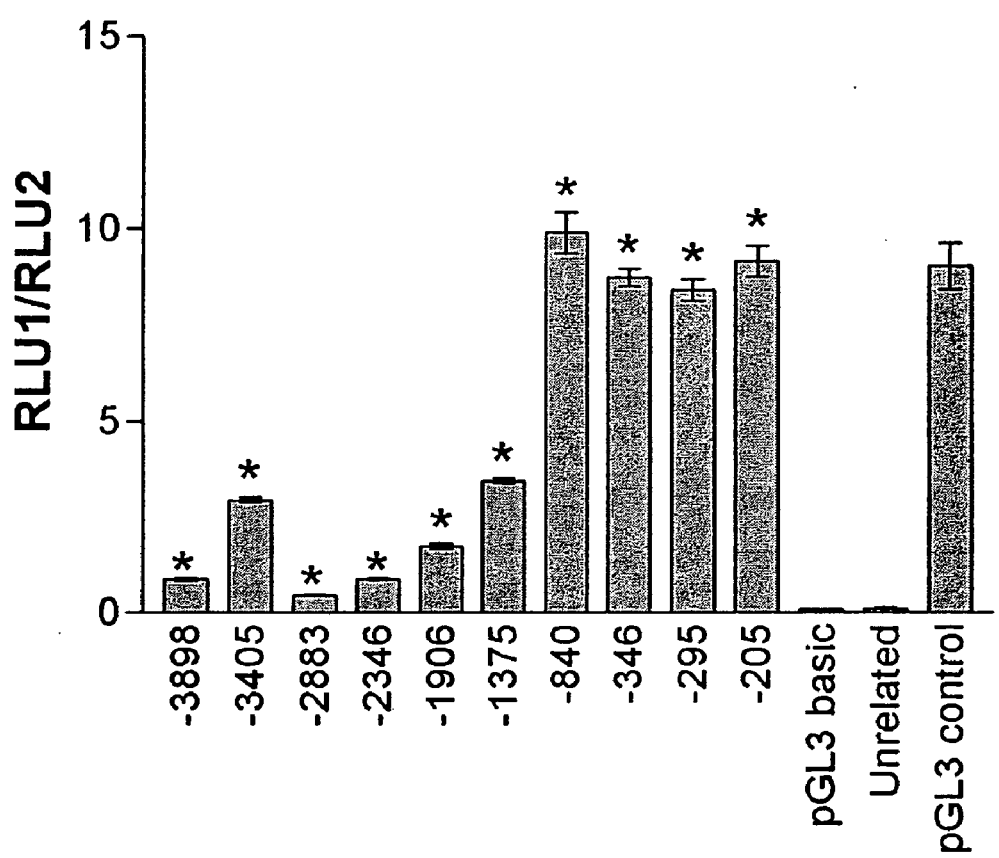
FIG. 4 shows basal expression from various $CRF_{2\alpha}$ receptor promoter fragments in A7R5 cells.

Our results in the A7R5 cultures indicate that the pattern of expression for the various constructs is very similar to that seen with the CHO-K1 cells (See FIG. 4). Distal regions of the $CRF_{2\alpha}$ promoter appear to exert an inhibitory influence that is gradually unmasked as the length of the promoter is shortened. Expression reaches a plateau that begins with the −840 construct and appears to last through the smallest promoter construct. 1-way ANOVA revealed a significant difference amongst constructs (F=221.9, P<0.0001). Planned pairwise comparisons using Student's t-tests indicated that all the constructs were significantly higher than the pGL3-basic control construct (*, p<0.0001 for all cases). Examination of the means indicate that our lowest level of expression (−2883 construct) is 354% greater than expression from the promoterless control vector (pGL3-basic) (mean−2883=0.473±0.011, mean pGL3-basic=0.104±0.016), and is 5% of the strong expression elicited by the SV40 promoter (pGL3-control) (mean−2883=0.473±0.011, mean pGL3-control=9.038±0.610). Our highest level of expression (−840 construct) is 9412% greater than expression from the promoterless control vector (pGL3-basic) (mean−840=9.903±0.532, mean pGL3-basic=0.104±0.016), and is 9.6% greater than the strong expression from the SV40 promoter (pGL3-control) (mean−840=9.903±0.532, mean pGL3-control=9.038±0.610). Furthermore, the unrelated human chromosomal DNA sequence (unrelated) was unable to drive expression above background. This data in the A7R5 cultures provides further evidence that our $CRF_{2\alpha}$ promoter constructs function and are appropriate tools to monitor $CRF_{2\alpha}$ specific transcription.

I. Characterization of Inducible Expression from Full-length $CRF_{2\alpha}$ Promoter A stated goal for the constructs is the ability to identify agents that can alter expression of the $CRF_{2\alpha}$ gene. Therefore, we designed experiments to demonstrate this ability. Using methods previously described in this application, CHO-K1 cultures were transfected with the −3898 construct and the pRL-TK internal control construct. These cultures were then treated with either CRF (1 μM), urocortin (1 μM), dexamethasone (1 μM), forskolin (10 μM), or the appropriate control at the time of transfection. The control for CRF and urocortin was culture media whereas the control for dexamethasone and forskolin was the culture media with the amount of DMSO required to solubilize these compounds. CRF and urocortin are ligands for the CRF receptors, dexamethasone stimulates the glucocorticoid pathway and forskolin increases intracellular cAMP levels. Twenty-four hours following transfection and treatment, the cultures were harvested a processed for luciferase assay as described previously in this application.

Figure 5:
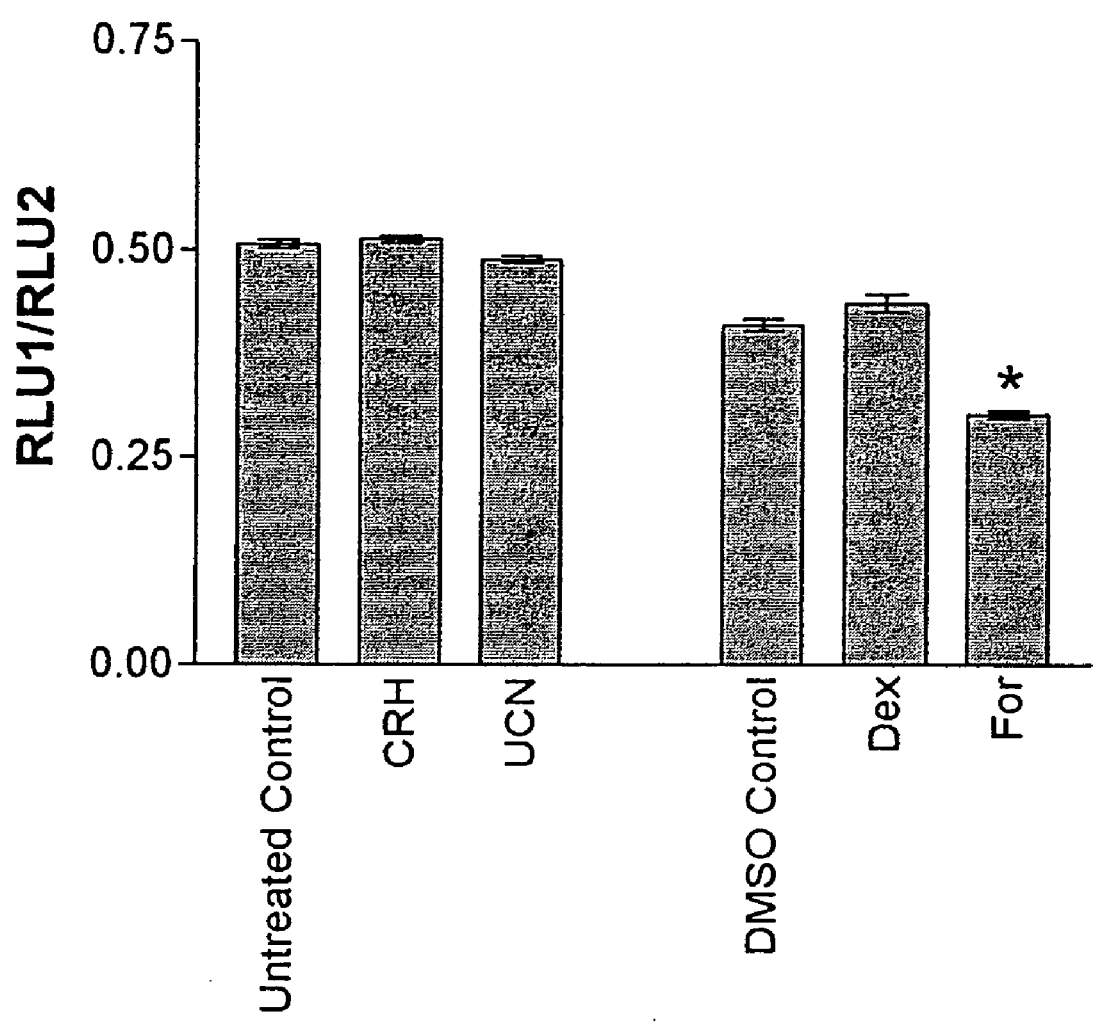
FIG. 5 shows the effects of various treatments on expression from the full-length $CRF_{2\alpha}$ receptor promoter in CHO-K1 cultures.

Statistical analysis was done on results from CHO-K1 cultures stimulated with the various compounds (See FIG. 5). Following demonstration of a main effect of treatment in a 1-factor ANOVA (F=668.1, *, p<0.0001), post-hoc analysis with Newman-Kuels multiple comparison test indicated that treatment of CHO-K1 cultures with CRF or urocortin did not significantly change expression compared with the untreated control cultures. This was expected because CHO-K1 cells do not express CRF receptors. Dexamethasone also does not appear to alter expression in the full-length $CRF_{2\alpha}$ promoter compared with the DMSO control cultures. However, forskolin treatment significantly lowers expression (*, p<0.001) compared with the DMSO control cultures (forskolin mean=0.302±0.012, DMSO control mean=0.411±0.004). This finding suggests that altering intracellular cAMP levels affects expression from the $CRF_{2\alpha}$ promoter. It should be noted that IBMX, an antagonist of phosphodiesterase activity, was not given to cultures receiving forskolin. The prolonged exposure to forskolin (24 hours) without IBMX may have lead to increased phosphodiesterase activity within the A7R5 and CHO-K1 cultures resulting in below normal levels of cAMP. Nonetheless, the results demonstrate the constructs ability to monitor agent induced changes in expression from the $CRF_{2\alpha}$ receptor promoter.

Using a similar experimental paradigm, we treated A7R5 cultures to determine what agents may alter expression from the $CRF_{2\alpha}$ promoter. In addition to treating the cultures with CRF and urocortin (1 μM each), A7R5 cultures also were treated with either of the antagonists alone D-Phe or DMP696 (1 μM each), CRF plus D-Phe (1 μM each), CRF plus DMP696 (1 μM each), urocortin plus D-Phe (1 μM each), and with urocortin plus DMP696 (1 μM each). D-Phe is a non-selective CRF receptor antagonist, blocking both CRF1 and CRF2 receptors, whereas DMP696 is specific to CRF1 receptors. A7R5 cultures are known to express CRF2 receptors and should be a highly appropriate cell type to monitor $CRF_{2\alpha}$ receptor expression.

Figure 6:
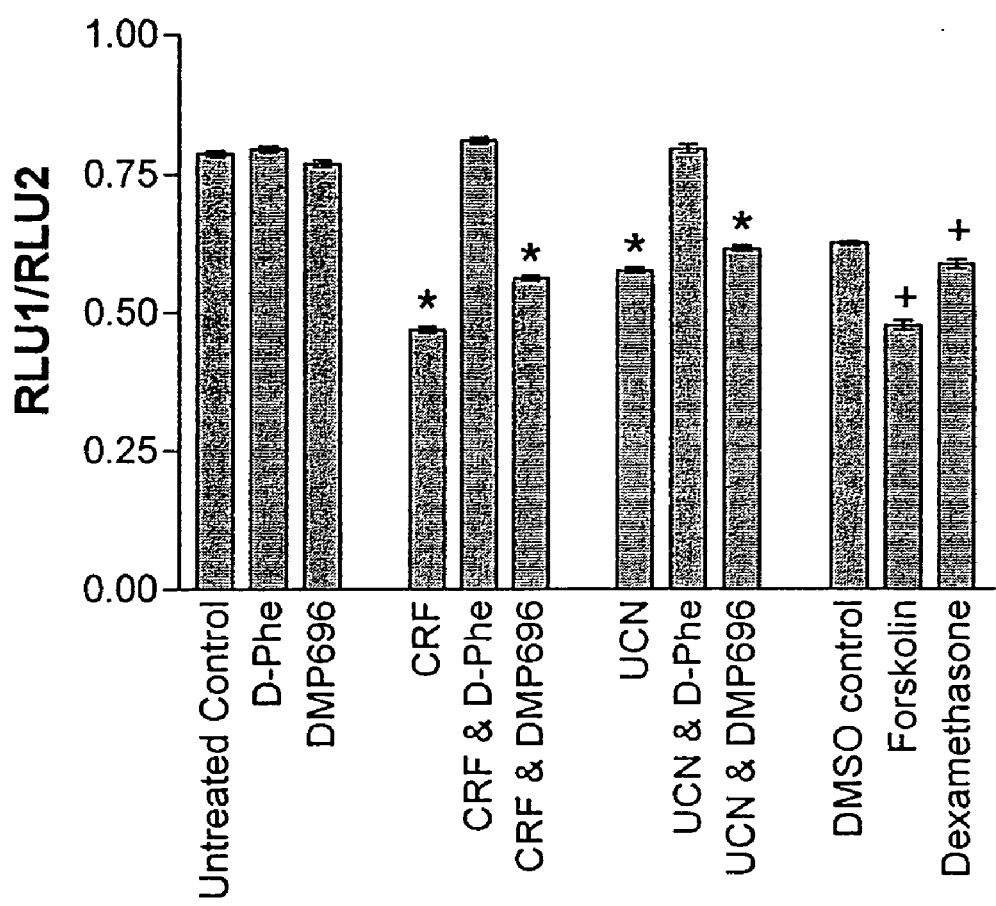
FIG. 6 shows the effects of various treatments on expression from the full-length $CRF_{2\alpha}$ receptor promoter in A7R5 cultures.

Analysis of the CRF and urocortin experiments with separate 2-factor ANOVAs revealed significant main effects of agonist and antagonist treatment and there was a significant agonist by antagonist interaction (See FIG. 6). Post-hoc analysis with a Bonferroni posttest revealed that CRF and urocortin significantly decrease expression from the −3898 construct as compared to the untreated control cultures in the A7R5 cultures (*, p<0.001 for both cases). The addition of the non-selective CRF receptor antagonist, D-Phe, with either CRF or urocortin brought expression from the full length promoter back to the levels seen in the untreated controls. However, the CRF1 receptor antagonist, DMP696, did not affect either the CRF or urocortin induced reduction in expression from the full length promoter. These results demonstrate that either CRF or urocortin can reduce expression from the −3898 $CRF_{2\alpha}$ receptor promoter construct within A7R5 cultures in a CRF2 receptor dependent manner.

In a separate experiment the effects of forskolin and dexamethasone were compared to DMSO control A7R5 cultures. Analysis with a 1-factor ANOVA revealed a significant main effect of treatment, and post-hoc analysis indicated that both forskolin and dexamethasone significantly reduced expression (FIG. 6, +, p<0.001) compared with the DMSO control cultures. These findings are consistent with those seen in the CHO-K1 cultures.

J. Characterization of Forskolin Induced Expression from $CRF_{2\alpha}$ Receptor Promoter Fragments In the present assay system each active test agent may produce its effect by interacting with one or more regulatory elements, or corresponding transcription factors, that are present in the promoter region. One of the advantages of having a series of constructs that contain sequentially smaller fragments of the promoter is that these constructs can be used to identify the region of the promoter where a test compound may be exerting its effect. This is achieved by identifying which of the promoter constructs respond to the test compound and which do not.

Figure 7:
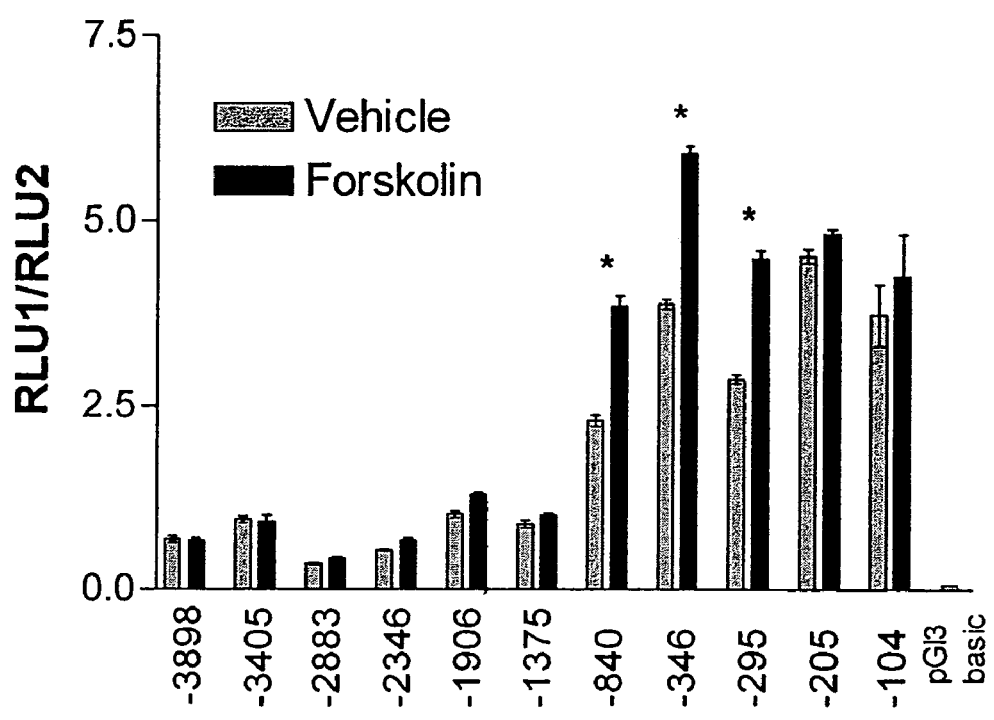
FIG. 7 shows the expression various $CRF_{2\alpha}$ receptor promoter fragments following 10 μM forskolin and 0.25 mM IBMX administration.

As a proof of this idea, we have examined the ability of forskolin to affect expression from all of the truncated fragments of the $CRF_{2\alpha}$ promoter. In these experiments, CHO-K1 cultures were transiently transfected with the $CRF_{2\alpha}$ promoter constructs. At the time of transfection, the cultures were either given vehicle or forskolin (10 μM) with IBMX (0.25 mM). Following twenty-four hours, the cultures were harvested for the luciferase assay as described above. 2-way ANOVA indicates there is a significant main effect of treatment and construct (See FIG. 7), and there is also a significant treatment by construct interaction (*, p<0.0001 for all three). Post-hoc analysis with a Bonferroni posttest revealed a significant forskolin-induced increase in expression when compared to the respective vehicle control cultures for three of the constructs (−840, −346 and −295; *, p<0.001). All other constructs did not show a significant forskolin-induced change in expression compared with the respective vehicle controls. These results suggest that a forskolin-induced increase in expression from the $CRF_{2\alpha}$ promoter is mediated through regulatory element(s) located somewhere between −840 and −205 bp relative to the putative TSP. These results demonstrate the ability of these promoter constructs to identify agents that alter expression driven by the promoter, and the ability of the same constructs to facilitate identification of the region of the promoter where these agents exert an effect.

K. Production of Transgenic Mice

In another embodiment, the present invention is a transgenic mouse comprising a heterologous promotor sequence for corticotropin releasing hormone receptors $CRF_{2\alpha}$. In one preferred embodiment, the transgenic mouse would be created as follows: Once potential therapeutic agents are identified in our cell culture model we will test their ability to alter CRF2 receptor promoter activity in transgenic animals. Reporter constructs that consist of the basal $CRF_{2\alpha}$ receptor promoter placed upstream of the enhanced green fluorescent protein or β-galactosidase will be used to generate transgenic mice. The procedure for generating the enhanced green flourescent construct has already been described, and the procedure for generating the β-galactosidase construct was identical to that used to make the firefly luciferase construct. These animals will allow us to confirm the appropriate spatial and temporal expression of the $CRF_{2\alpha}$ receptor promoter.

The reporter constructs will be identical to those described above and will preferably consist of 3898 bp of human CRF2α receptor promoter or 4693 bp of rat $CRF_{2\alpha}$ receptor promoter fused to the coding region of EGFP or β-galactosidase. Transgenic animals will be generated using standard techniques. The preferred technique would involve the microinjection of 100 copies of the promoter-reporter construct into the male pronucleus of a fertilized egg. Injected eggs are then transplanted into pseudo-pregnant females and the progeny from these transplantations examined for the presence of the $CRF_{2\alpha}$ receptor promoter-reporter construct (called "the transgene"). Animals containing the transgene will be identified by extracting DNA from a small amount of tail tissue and probing this DNA with a segment of the EGFP or β-galactosidase gene, which is not normally found in the mammalian genome. Animals that contain the $CRF_{2\alpha}$ receptor promoter-reporter transgene will be mated to normal animals so that transgenic lines are established. Preferably, we will generate three transgenic lines that contain the transgene in three separate sites within the genome. In this way we will verify that the expression patterns we observe are a result of EGPF or β-galactosidase expression from our promoter segment and are not due to site insertion effects.

To confirm the appropriate function and expression of the $CRF_{2\alpha}$ receptor promoter-reporter transgene, the following will preferably be performed: Brain tissue sections will be taken from transgenic animals beginning in late embryonic development and extending at five-day intervals into adulthood (postnatal day 60). Sections will then be observed under 488 nm light or 420 nm light to identify those brain cells that express EGFP or β-galactosidase, respectively. The pattern of reporter expression will be compared with the normal pattern of $CRF_{2\alpha}$ receptor expression. The expression of the $CRF_{2\alpha}$ receptor promoter transgene should overlap with expression of the endogenous $CRF_{2\alpha}$ receptor gene both temporally (i.e., it should begin to expressed when CRF2α receptor is first expressed) and spatially (i.e., expression of the transgene should be confined to those cells within septum and ventromedial hypothalamus that normally express $CRF_{2\alpha}$ receptor).

L. Use of Transformed Cell Lines and Transgenic Animals

Cells transfected with $CRF_{2\alpha}$ receptor promoter regions fused to a reporter construct will allow the testing of potential therapeutics. Pharmacologically relevant amounts of candidate small molecules will be applied to the transfected cells in the media and the influence of these molecules on reporter gene expression levels will be assessed by the methods discussed above. These experiments will be replicated at least 10 times and any small molecule that yields a statistically significant difference in expression will be considered a positive find. The level of reporter expression after treatment with a specific candidate drug will enable the determination of the degree to which the drug is influencing $CRF_{2\alpha}$ receptor activity.

Candidates that increase the expression of CRF2 promoter-reporter activity can then be further tested in vivo. Transgenic animals will be treated with the candidate drug to determine whether $CRF_{2\alpha}$ promoter-reporter transgene levels are elevated in the same way and to the same degree as that found in the cells lines. Adverse drug effects can also be determined with these animals.

If the drug behaves similarly in vivo and there are no signs of significant toxicity, then the drug could be tested in a variety of animal models that are predictive of antidepressant or anti-anxiety activity. If the candidates are active in these tests they could serve as therapeutic agents in psychiatric disorders, such as depression.

REFERENCES

Arborelius L, Owens M J, Plotsky P M, Nemeroff C B (1999) The role of corticotropin-releasing factor in depression and anxiety disorders. *J Endocrinol* 160:1-12.

Baker D G, West S A, Nicholson W E, Ekhator N N, Kasckow J W, Hill K K, Bruce A B, Orth D N, Geracioti T D, Jr. (1999) Serial CSF corticotropin-releasing hormone levels and adrenocortical activity in combat veterans with post-traumatic stress disorder. *Am J Psychiatry* 156:585-588.

Bakshi V P, Smith-Roe S, Newman S M, Grigoriadis D E, Kalin N H (2002) Reduction of stress-induced behavior by antagonism of corticotropin-releasing hormone 2 (CRH2) receptors in lateral septum or CRH1 receptors in amygdala. *J Neurosci* 22:2926-2935.

Beglinger C, Degen L (2002) Role of thyrotrophin releasing hormone and corticotrophin releasing factor in stress related alterations of gastrointestinal motor function. *Gut* 51 Suppl 1:145-149.

Bremner J D, Licinio J, Darnell A, Krystal J H, Owens M J, Southwick S M, Nemeroff C B, Charney D S (1997) Elevated CSF corticotropin-releasing factor concentrations in posttraumatic stress disorder. *Am J Psychiatry* 154:624-629.

Chappell P, Leckman J, Goodman W, Bissette G, Pauls D, Anderson G, Riddle M, Scahill L, McDougle C, Cohen D (1996) Elevated cerebrospinal fluid corticotropin-releasing factor in Tourette's syndrome: comparison to obsessive compulsive disorder and normal controls. *Biol Psychiatry* 39:776-783.

Chen R, Lewis K A, Perrin M H, Vale W W (1993) Expression cloning of a human corticotropin-releasing-factor receptor. *Proc Natl Acad Sci USA* 90:8967-8971.

Coste S C, Quintos R F, Stenzel-Poore M P (2002) Corticotropin-releasing hormone-related peptides and receptors. Emergent regulators of cardiovascular adaptations to stress. *Trends Cardiovasc Med* 12:176-182.

Fossey M D, Lydiard R B, Ballenger J C, Laraia M T, Bissette G, Nemeroff C B (1996) Cerebrospinal fluid corticotropin-releasing factor concentrations in patients with anxiety disorders and normal comparison subjects. *Biol Psychiatry* 39:703-707.

Guillemin R, Rosenberg B (1955) Humoral hypothalamic control of anterior pituitary: a study with combined tissue cultures. *Endocrinology* 57:599-607.

Heinemeyer T, Chen X, Karas H, Kel A E, Kel O V, Liebich I, Meinhardt T, Reuter I, Schacherer F, Wingender E (1999) Expanding the TRANSFAC database towards an expert system of regulatory molecular mechanisms. *Nucleic Acids Res* 27:318-322.

Kostich W A, Chen A, Sperle K, Largent B L (1998) Molecular identification and analysis of a novel human corticotropin-releasing factor (CRF) receptor: the CRF2gamma receptor. *Mol Endocrinol* 12:1077-1085.

Lewis K, Li C, Perrin M H, Blount A, Kunitake K, Donaldson C, Vaughan J, Reyes T M, Gulyas J, Fischer W, Bilezikjian L, Rivier J, Sawchenko P E, Vale W W (2001) Identification of urocortin III, an additional member of the corticotropin-releasing factor (CRF) family with high affinity for the CRF2 receptor. *Proc Natl Acad Sci USA* 98:7570-7575.

Lovenberg T W, Liaw C W, Grigoriadis D E, Clevenger W, Chalmers D T, DeSouza E B, Oltersdorf T (1995a) Cloning and characterization of a functionally distinct corticotropin-releasing factor receptor subtype from rat brain. *Proc Natl Acad Sci USA* 92:836-840.

Lovenberg T W, Liaw C W, Grigoriadis D E, Clevenger W, Chalmers D T, De Souza E B, Oltersdorf T (1995b) Cloning and characterization of a functionally distinct corticotropin-releasing factor receptor subtype from rat brain. *Proc Natl Acad Sci USA* 92:836-840.

McGaugh J L, Roozendaal B (2002) Role of adrenal stress hormones in forming lasting memories in the brain. *Curr Opin Neurobiol* 12:205-210.

Mitchell A J (1998) The role of corticotropin releasing factor in depressive illness: a critical review. *Neurosci Biobehav Rev* 22:635-651.

Nemeroff C B (1989) Clinical Significance of Psychoneuroendocrinology in Psychiatry: Focus on the Thyroid and Adrenal. *J Clin Psychiatry* 50:13-20.

Perrin M H, Sutton S, Gulyas J, Lovejoy D, Rivier J E, Vale W W (1995) Development of an Improved Ligand for CRF Receptor Characterization Using a Radiolabelled CRF Antagonist. Society for Neuroscience-ABSTRACT ONLY 21:1390.

Potter E, Behan D P, Fischer W H, Linton E A, Lowry P J, Vale W W (1991) Cloning and characterization of the cDNAs for human and rat corticotropin releasing factor-binding proteins. *Nature* 349:423-425.

Quandt K, Frech K, Karas H, Wingender E, Werner T (1995) MatInd and MatInspector: new fast and versatile tools for detection of consensus matches in nucleotide sequence data. *Nucleic Acids Res* 23:4878-4884.

Reul J M, Holsboer F (2002) Corticotropin-releasing factor receptors 1 and 2 in anxiety and depression. *Curr Opin Pharmacol* 2:23-33.

Reyes T M, Lewis K, Perrin M H, Kunitake K S, Vaughan J, Arias C A, Hogenesch J B, Gulyas J, Rivier J, Vale W W, Sawchenko P E (2001) Urocortin II: A member of the corticotropin-releasing factor (CRF) neuropeptide family that is selectively bound by type 2 CRF receptors. *Proc Natl Acad Sci USA* 98:2843-2848.

Tache Y, Martinez V, Million M, Wang L (2001) Stress and the gastrointestinal tract III. Stress-related alterations of gut motor function: role of brain corticotropin-releasing factor receptors. *Am J Physiol Gastrointest Liver Physiol* 280: G173-177.

Takahashi L K (2001) Role of CRF(1) and CRF(2) receptors in fear and anxiety. *Neurosci Biobehav Rev* 25:627-636.

Takahashi L K, Ho S P, Livanov V, Graciani N, Arneric S P (2001) Antagonism of CRF(2) receptors produces anxiolytic behavior in animal models of anxiety. *Brain Res* 902:135-142.

Vanitallie T B (2002) Stress: A risk factor for serious illness. *Metabolism* 51:40-45.

Vaughan J, Donaldson C, Bittencourt J, Perrin M H, Lewis K, Sutton S, Chan R, Turnbull A V, Lovejoy D, Rivier C, et al. (1995) Urocortin, a mammalian neuropeptide related to fish urotensin I and to corticotropin-releasing factor. *Nature* 378:287-292.

Veith R C, Lewis N, Langohr J I, Murburg M M, Ashleigh E A, Castillo S, Peskind E R, Pascualy M, Bissette G, Nemeroff C B, Raskind M A (1993) Effect of desipramine on cerebrospinal fluid concentrations of corticotropin-releasing factor in human subjects. *Psychiatry Res* 46:1-8.

Zobel A W, Nickel T, Kunzel H E, Ackl N, Sonntag A, Ising M, Holsboer F (2000) Effects of the high-affinity corticotropin-releasing hormone receptor 1 antagonist R121919 in major depression: the first 20 patients treated. *J Psychiatr Res* 34:171-181.

---

We claim:

1. An in vitro method for identifying an agent that can alter the activity of the human CRF$_{2\alpha}$ receptor promoter, the method comprising the steps of:
   (a) providing a host cell in vitro that comprises a vector comprising a polynucleotide and a heterologous reporter gene operably linked to the polynucleotide, the polynucleotide being selected from the group consisting of nucleotides 46 to 3943 of SEQ ID NO:2, nucleotides 539 to 3943 of SEQ ID NO:2, nucleotides 1061 to 3943 of SEQ ID NO:2, nucleotides 1598 to 3943 of SEQ ID NO:2, nucleotides 2038 to 3943 of SEQ ID NO:2, nucleotides 2569 to 3943 of SEQ ID NO:2, nucleotides 3104 to 3943 of SEQ ID NO:2, nucleotides 3598 to 3943 of SEQ ID NO:2, nucleotides 3649 to 3943 of SEQ ID NO:2, nucleotides 3739 to 3943 of SEQ ID NO:2, and nucleotides 3840 to 3943 of SEQ ID NO:2;
   (b) exposing the cell to a test agent; and
   (c) measuring and comparing the reporter gene expression level to that of a control cell that is not exposed to the test agent wherein a higher or lower expression level than that of the control cell indicates that the agent can alter the activity of the human CRF$_{2\alpha}$ receptor promoter.

2. An in vitro method for identifying an agent that can alter the activity of the human CRF$_{2\alpha}$ receptor promoter, the method comprising the steps of:
   (a) providing a host cell in vitro that comprise a vector comprising a functional fragment of the human CRF$_{2\alpha}$ receptor promoter comprising SEQ ID NO:2 and a heterologous reporter gene operably linked to the functional fragment;
(b) exposing the cell to a test agent; and
(c) measuring and comparing the reporter gene expression level to that of a control cell that is not exposed to the test agent wherein a higher or lower expression level than that of the control cell indicates that the agent can alter the activity of the human $CRF_{2\alpha}$ receptor promoter.

* * * * *

SEQUENCE LISTING

```
<160> NUMBER OF SEQ ID NOS: 2

<210> SEQ ID NO 1
<211> LENGTH: 5011
<212> TYPE: DNA
<213> ORGANISM: rat

<400> SEQUENCE: 1
agacccaatt aagaccacat tctgaggtat taggactttg aaatgcagtg tgaaagcttg      60
gaggggcagc atttagtcta tgtcagtttc ttcatccatt agagaaagtt agggttgaag     120
tctatctaaa aggcacactt tggcagaggg gacagacagc atgggccatg cctagcagac     180
ataggcagga tgagatggag gccccttact tcaggagtgc catcccttcc ttcacttttt     240
cattggagga aacactgctg ttcaaagaca ccctggcctc tccctgtctt ccctgcccag     300
atgtttagaa aggtggcaca gatgtcccac ccccaacttg agttgaggga gaaagtcctc     360
ctcttggaca cctgccttcc ctgcctaatt tttagggcct atgtctgctg acaaaacaca     420
cctgaactaa atttaaacaa aatttggttg aaaaatcttt ttgactcata aggtaagagc     480
tcattaactc acagcacagc agttttgaca gtaccttgag tccctgataa gttcctcgtc     540
cacagagcct caccttgctt gtttgttttt tatttattt tattttttga ggtcttttgg     600
cttttcactt tgctttgttt tcgccagaag caagctgtga ttgtggccat ggctttctaa     660
cctgtgcttc tctctaataa ctgagagtga atgcttcctt gtgtcattaa atattcatcc     720
```

-continued

```
agtgcgtcgc tggtgacgct gcctagcagc cactgtgagg acacatcacc cctcattagc    780
cacggccctg gggtggacat gggaactgtt aggatgcctg ctgggctgca gaaattgctt    840
ctgttgtccc cacatgggag cagtctcttc tcttgtgtcc actagttagg agaatgtgga    900
attgactaag aagtgcaaaa taaagcaaaa ctgcgctcac catccttcag agactcttac    960
attcgaacac ctgaaaagga agaaaaagga gcaggggga acaaatgcaa ccttcaagac    1020
agcgcttcct ccgggaaggc acctgtgggc ctgactgcta atatctgttc cattgggcgg    1080
ccagctcatt atggtcactg ctatacaaag gcctccatta agaaatgac cataaaacaa    1140
gtttagtcca tgtgtatgtg ggctgatgat gacaagggac tgtaaatcaa aggctatgac    1200
caattgtgct gtatgcccct gtggtccaaa taaatgaaac aatccacaga gtcaggagag    1260
caattataac ttccagcaag attttaatgg aatgtttcta ttttattcat cacacatgca    1320
tttatatata tttgaaaaat gctagggaat tattgggagg catattattt attctattca    1380
gagacaatat aagggtccag aggcatccaa ggaatctttt aagtaacttt ccagtccaag    1440
atgcatggct actcatacac aaagacactc atgtgtgcac acacaggaag gcatactatg    1500
attagagggg aagggagcct ggccaggcag atagaaccct gggttttcct cagccctgtg    1560
gctaaggagc ctgtttggtt cttttgatgt ttgtttgttg gtttgttggt ttgttttccc    1620
atgtgatgga taccatctct ggagcattct gatgggtgtt ggggactctg gggaaaatta    1680
ggcttgccca cccatggaac ctcaggtggg tagagttggc taagtccggg ttggtagagc    1740
tttagtgaga cctagagcag ccctatgac tagggaagcc tcttgagcag taagggcaga    1800
agaggtaaga ccacagttgc atgcttgcag gaagaggaaa agaagctgca gagttgaagg    1860
gaattctaaa tggcgggaga ccttggctaa agcacagagg gctcagccag caacagagtg    1920
aagatggggg atgggcttca ccaagtgtct tctttatagt gccaaagaca ctggctccat    1980
cctggaggct gtgcggagct aaatgtggaa gtaagacgac gtgaccacaa ttgcaaagtc    2040
tttccatctt ccctatgaag gaaatgggaa gccggctgtg gtgccgcaga gatgagcaca    2100
gctggcagac tggcacaggg aactggcttt ccttctctgc gtgtctggac agtgcatatg    2160
tgggtgggat tatcactaca gccttcctg gtcctgcagc atggatccat tgttgaacat    2220
ccggacacca tgtcatctcc tctgttctta ggcagagtta ggggaggtat gacctggagc    2280
atccctcaat gtcatagttt aagagagttg ctccacacct cactataact cccagaataa    2340
gatggcattg cttgtcctta gccatcccta aaaagacttc ctgtgtacac cctgtcatgg    2400
agggcagcct ctcacagaag caacggctaa ccctataagc cttgttgtcc acttggcact    2460
tgcatggttg gggcgtgaa tgagagcatg cgtagttttg cctgagtgca gcactctgac    2520
agtagtgtct gtgggctctg caggcctatt taatggcatg gatgggctg tgcagtggat    2580
gtgtctaagc tggcctagca ttattcatca ccaccatagc ttctattagt ggtgacccaa    2640
gatgtgagac actgagtagc agaaacacat ccctcagccc aattcctcat gacaacaggg    2700
ccctccctgg cacctgatcc acttccctga acctaccctg cagtgttcct ggccccacta    2760
ggctgaaatg tacctacttt ccaaatatgt gtcctttcat gcctagcttg ggtctaccat    2820
aggactgact ggaagcctca gggacctctg tccacccccc tcttcctctt tactaaacag    2880
cctccacctt gcttgtatag agctgggtct aacctaagga aagccatctt gccatttctg    2940
catttgcccc cttgcgagca ttagagtgag ctgtgaagcc agttggtttc cctacttaac    3000
atcacgaatc atgtaccagc tgtgcctgta aacatgatat tatgaagaaa tggtgacatg    3060
```

```
tcctaggatc ctagaggtct taagtattca tacatttagg gtgcacagta gcttttggtc    3120
ctgacactga agtggtcact ttccagagga aactctgtca agcaagcaag tcacccagtc    3180
cctattctgt agaaatctgc atgtaaaagg gtaggtcaga agtgctcacc acctccttac    3240
tgtggtatgt gtctcctgag ccatggctct gattaggaat aaagtcaccc ggggctgggg    3300
atttagctca gtggtagagt gctaggaggc gcaaggccct gggttcggtc cccagctccg    3360
aaaaaaagaa ccaaaaaaaa aaaaaaaaaa aggaataaag tcacccttg cacttgaatt     3420 ggtttccttc ttctctgtgc tatgacagta tatgaagggc catcctttgc tagtgaagga    3480
gactgcatcc ctgtgaggac ggactcagcc agtcatgctc agacctaaga ctgccgagat    3540
ttggaccgga gtcccaactg tccatccagg aggcagagga cagatctatc tggtagtctg    3600
tctccctgcc agttggcagg tcctagagag agtccagggc tcagtctggt cttaccactt    3660
gctcagtctc tcacaaactc acttgctgtg cgagggaatg agggcaccat taatatggag    3720
gctaggaaga ctgtacaaaa gcaatggcaa gttctttgga ggaccggcct ctttaggggg    3780
gctttggcct tcactagcac ctggtcccct atggagggtg caggaggact ggactggttc    3840
tagaccctct tacaccatgt ctatagatgc tctggactgt gaaggaactc agaaaacatg    3900
ccactggtgg agaaaagtca ggaaggctct tgcctcaggc aacatgacag aaaagagagg    3960
caaaaccgca tccagactgg aaaaaaaaaa cacctaggca ggttcctcaa cctaggccca    4020
tccacagtta taggcccacc ctgagcactc tacagggtgc tcacccctcc attcttgtga    4080
cttttctcca ctcctcagat agccctgctt aagccaggag aaagagacct gttttcacct    4140
ctcactctat ctggtgccca ggatactaaa accatcaagt cttccagata attttaatta    4200
atgtcttcct agatattctc atctcgctgc tggtggcaaa tctgccggtg tgaaatctgg    4260
cgttgtcacc agttcctggc tcctgctgag agccatctac ctactccata ttttctccat    4320
ctctcttaga ccctctctgg taaactgtct gcaaccctcc ggggcccctt caatccattt    4380
tcttccccag ggcacaaatc tgctgctggg ccgacttgtt gccctatcc atctctagtg     4440 tactcctttg ggaggataaa tttcagggtc aggagcagac caactttggc tggcaacggg    4500
tgtaggaagg tggtgtggat ttcctgtaga cccgaggcct gcgaccctcg atcctcggac    4560
gggttattag ccaccccaga ccgtagatcg tcagccctgc caccattcca gagacttctc    4620
tggtcaagag agcaccgacg gggctggaga tagagccccg ccccgacgc cgctattggt      4680 catggtcgag caggcggccc ctcatctccg tgagccccga ggcttctctt ggccaaggtc    4740
ctaggagtga tccgattgag agcggcgccc caaagctgcc gggctggccg gggtgggcgg    4800
ggaggcacct ggacgctgca ctctctggtg gctccgcgtc gcgccaggtc cctcgcagcc    4860
acgcggggcg cgcactccca ctcccaacgc gcgcggctcc ggagcgcaat ggacgcggcg    4920
ctgctcctca gcctgctgga ggccaactgc agcctggcac tggccgaaga gctgcttttg    4980
gacggctggg gagagccccc ggaccccgaa g                                    5011

<210> SEQ ID NO 2
<211> LENGTH: 4272
<212> TYPE: DNA
<213> ORGANISM: Human

<400> SEQUENCE: 2
atgggaagag agccttggcc tgaagacagg gacctgggct ttcctcagct cttctgccaa      60
ggtatctgtc ctttcttagt gactcactgg gctgaagtct agagcattcc aatgggtgct     120
ggggatgggt tagtgaacca ggaccagccc tgcccttggg gaggcatggg ctggtagatg     180
```

-continued

```
agacaatgaa taaaaagcaa cctggatgtg acataggcca gcacccagca gatggggtca      240
ccaaggagct gcatgtctga aggatgagtg tggagctgta aggccatttc cagtgcagaa      300
atacaaacaa ggaacagaga tagcgaatgg tttctggtag tgacacattg ttctggaggg      360
cctttcaaat gaagcaggag ggtgaggatg gggacgatg atcatgaaga accttctttg       420
caataccaaa gatggttccc aggaatgaca tgttgttctg gagggccttt caaatggagc      480
agaagggtga ggatgaggga tagatgatta cgaaggacct tctttgcaat accaaagagg      540
tggtctccat ctcaagggca atgggttggc ggcactccta tgaggaagag tgacaggatc      600
gtaattataa aacatcgttt tatctgccat gaggagacag ggagcccatt tgggctgctg      660
cagagatgag gatggcctgg gagaagtaag ggagggaaac ctcttttgct tgtctgggaa      720
tcctattgtc catctgtaaa acaagaatgt gggattggat gtcactgaga gtcctttctg      780
tccccacagc ttagtcccat ggtttgacat gaagacacca ggccaattcc tctgtcctgc      840
agtggagtag ataggggtga ggaggggtg cctggcctgg gacccctgtc tccagtgcta      900
cagggcaaaa gtgcagcacc ttcaggcccc tctggaacct ctgtgccctc agcaaccccg      960
tcgtaattcc caggaaacac cacgactatt ccagctgtgc ctgaatagac tccctctcta     1020
tgtagtctaa ccaaggacag tcccttagag aagcaaagat gcatcctgtc cctttaaatc     1080
ctgttttcca gctgacattt gagtggtagg ggatgaatta gagagagaat gtgtgtgcat     1140
ggtgaagatg cataactgtg gctctgtgtg tgattctgtt gtgcctacat gcctgtttga     1200
tgccatgtat taggctttgc aagtgtgtct gagctggcct ggaactgtcc actgctgctg     1260
cagctgacat cagaggtggg ccatgggatg ggatgcaggg caccagaggc acctgcctta     1320
ctctgctgct catggtacac aggggtcttc caaagtacct gtcacacttc cctgaaccta     1380
tttgccaacc tgtccccaac agcttgggga cacacaaact gttccaaata cttatcccct     1440
aattcctggc ctccagctgg gatggggctg gcctgcagcg ctgggaaccc atcactatcc     1500
caaagcctct aatctacctc tgcttcttta gttagcaaaa atgcccctgt ctttgtttgt     1560
ttgtacttgg atttagtaaa attgagggaa ttttgggggct cttcccaatt tcttcctcat     1620
ttgcctgttt gcagacacta aagtgagctg taaaatcaat ttgttcccaa actgctacct     1680
tttctagttt tccctctgtc acatctcgaa tgacaactgt gcctataata ataagatcca     1740
tgaagaaatg gccccacatc caggggacct cgggtctgtg ggtctgtggg tatgtgctca     1800
gaccccaact gctcattcag gatgcagaac agcctttgac tctgccactg aaatggtcac     1860
ttcccagaag aatctttggt atgtgagctc tcccagttaa gagcaatcca gttcacccag     1920
gccaaccctc tgttctgcag aaatctgcat gagatgagaa gtccctggcc tctggtcatt     1980
gggagcacac cacctcttga catagctgca tctataggtg ctttaggcac cacctaggtg     2040
gtggctgcag taatgaacaa ggataataac ttaagcttgg cttaggattt ctcccttcct     2100
ctgtgctgca ccgtgctgtg tgaagggcta tcccttgtat atgagggaca ctattgccct     2160
gtgaatacat gggctgacct ggccagccac cctctggcct gtgtgggacc ctgggtaaca     2220
gggctcagtc taggagcgga gggtaggact ctgcctaggt cctcccctgc tcctggcact     2280
ggataatatg aagaccaagg aacctctacc tctgcagctg cccagagctg agcctgggct     2340
ctcactgtcc attcaggagg cagagggtag acctggctgg ctgctcagca tcttgttcct     2400
gccagtcagc aggccctgga gagattccag ggctcagccc tggtcttagt gtggtctcac     2460
tcgctctgcc tgggcagtga cagcaccatt aatatggagg ctggtgagag cggagcacac     2520
```

```
aaaagcagcc tgcctgctgc tttgcctctc tctgcccagg gcatggtgct agttcatggt    2580
ggtttcagcc tttcctagca gcttaggttt atgtggagga tggcagggga acaggactgg    2640
tttctgagac taggttccag ctctccttgc cctctaaaga tagaaacaaa caacacacaa    2700
cacacatgta tgtcttcccc agactctccg tctcataact cagaaccaga gagtctcaga    2760
gctgagaggg gcctcgggga agatttcact gatggagaaa gctccagaag agagggcaag    2820
catcctgcct ggggtaccat ggcagggaga gcagagtcag aggctggacc aaaatgcagc    2880
ctgagtggaa gcatgcctta ccccaggccc tgcttcccga gcccaatgcc ccactcagct    2940
ggcagacaca gcaggcccgc cctgggcact ctgagggtgc agccacagca gatcaccaag    3000
gaggcattct gggccagggt ggggtggggg gcctgggcaa gttctctggg gaggtttcca    3060
gctcctccac acctgctgtg gggcctgatt ctccccgccc ctgccccgct actggtgtgg    3120
aaaccagggt caggtgaagc cctgcccaag ccttgaggaa gagagacaca ttctcacttc    3180
ttcctttatt ctttctggtg cccaaggcac taacaactgg gtgtataaag ccttccagat    3240
aatttcagcc aatttctccc ctagacttac tccatctgat taaatggcca cccagtcact    3300
caagcaggag acctgatgtt atccctgcct ctgggctcct acttaaaacc agccacccac    3360
tccagttcct cctcaccagg tctggctgcc cctccgaaat ctctctccat tccagcttcc    3420
acggtctgat ccaaggactt caacccactc aggccacttg atctcattag actcatgggt    3480
gtctccctgc ttccctccag gcctcctcga tacatttcct tcccagaggc tatggaggct    3540
tttggaggat gcagatctgc ccatgggctc tccgtctctg cctccctcca gtgtcctcgc    3600
tcagggaggg gaagctcagg cggaaagctg ccgaactttg ggttgcggct gtccctcgat    3660
tagcagagct gcggtgttct cctcgggcag gcgggcaggt gggcgcgctt tgctgccccc    3720
tgcagctcgg gggcctgcga tccccgcaca gagcattccg tcacccagg  cccacgctct    3780 ccagcccacc gccctcctct ggacgccgcg agtggaagag agctgcgaac tgagaagccg    3840
tactttgggc agggtggagg gcccgggggc tggagactga gcccctccga gaggagccgc    3900
ccggccccgc ccccggcgc agccattggc cgcggcggag cggctgtacc cgcagctccg     3960
tgcactcggc ggctcctctc cgggaaggtc cccacttgac agctctgggc gaccggaggt    4020
ggcgcccaaa ggctgcccgg gagatcgggg ctgggctggc gggggccagg accccgcgcc    4080
ctctcggccg ctcactctcg cgtccactcc ctcgcagtca cgccgggcgc gcactcccac    4140
tccctctccg cacgcggctg cgggacgcga tggacgcggc actgctccac agcctgctgg    4200
aggccaactg cagcctggcg ctggctgaag agctgctctt ggacggctgg gggccacccc    4260
tggaccccga gg                                                        4272
```